United States Patent
Chang et al.

(10) Patent No.: US 9,423,395 B2
(45) Date of Patent: Aug. 23, 2016

(54) FLUORESCENT CELL CYCLE PROBE HAVING M-PHASE SPECIFICITY

(71) Applicants: National University of Singapore, Singapore (SG); Agency for Science, Technology and Research, Singapore (SG)

(72) Inventors: Young-Tae Chang, Singapore (SG); Duanting Zhai, Singapore (SG); Sung-Chan Lee, Singapore (SG); Seong-Wook Yun, Singapore (SG); Yun-Mi Jeong, Singapore (SG); Nam-Young Kang, Singapore (SG); Sung-Jin Park, Singapore (SG)

(73) Assignees: National University of Singapore, Singapore (SG); Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/759,015

(22) PCT Filed: Jan. 14, 2014

(86) PCT No.: PCT/SG2014/000009
§ 371 (c)(1),
(2) Date: Jul. 2, 2015

(87) PCT Pub. No.: WO2014/109713
PCT Pub. Date: Jul. 17, 2014

(65) Prior Publication Data
US 2015/0355168 A1    Dec. 10, 2015

Related U.S. Application Data

(60) Provisional application No. 61/752,125, filed on Jan. 14, 2013.

(51) Int. Cl.
| | | |
|---|---|---|
| *G01N 33/50* | (2006.01) | |
| *C07F 5/02* | (2006.01) | |
| *G01N 33/58* | (2006.01) | |
| *C09B 23/01* | (2006.01) | |
| *C09B 23/04* | (2006.01) | |

(52) U.S. Cl.
CPC ............ *G01N 33/5091* (2013.01); *C07F 5/022* (2013.01); *C09B 23/0075* (2013.01); *C09B 23/04* (2013.01); *G01N 33/5005* (2013.01); *G01N 33/582* (2013.01)

(58) Field of Classification Search
CPC ............................ G01N 33/5091; C07F 5/022
See application file for complete search history.

(56) References Cited

FOREIGN PATENT DOCUMENTS

WO    WO 2012/071012 A2    5/2012
WO    WO 2012/173575 A1    12/2012

OTHER PUBLICATIONS

Zaragoza Dorwald (Side Reactions in Organic Synthesis, 2005, WILEY-VCH Verlag GmbH & Co. KGaA, Weinheim, Preface. p. IX.*
Zhai et al, ACS Combinatorial Science, Synthesis of a Novel BODIPY Library and Its Application in the Discovery of a Fructose Sensor, 2012, 14, pp. 81-84.*
Crosio, C., et al. "Mitotic Phosphorylation of Histone H3: Spatio-Temporal Regulation by Mammalian Aurora Kinases", *Mol. Cell. Biol.* (Feb. 2002), 22(3): 874-885.
Hadjantonakis, A.-K. and Papaioannou, V.E., "Dynamic in Vivo Imaging and Cell Tracking Using a Histone Fluorescent Protein Fusion in Mice", *BMC Biotechnology*, 4(33): 14 pages. (2004).
Hesse, M., et al., "Direct Visualization of Cell Division Using High-Resolution Imaging of M-Phase of the Cell Cycle", *Nature Communications*, 3(1076): 12 pages. (2012).
Jeong, Y.-M., et al., "CDy6, A Photostable Probe for Long-Term Real-Time Visualization of Mitosis and Proliferating Cells", *Chemistry & Biology*, 22:1-9 (2015).
Kanda T., et al., "Histone-GFP fusion protein enables sensitive analysis of chromosome dynamics in living mammalian cells", *Curr. Biol.* (Mar. 10, 1998), 8(7): 377-385.
Karolin, J., et al., "Fluorescence and Absorption Spectroscopic Properties of Dipyrrometheneboron Difluoride (BODIPY) Dreivatives in Liquids, Lipid Membranes, and Protiens", *J. Am. Chem. Soc.* 1994, 116, 7801-7806.
Vleugel, M., et al., "Evolution and Function of the Mitotic Checkpoint", *Development Cell*, 23:239-250 (2012).
Notification of Transmittal of the International Search Report and the Written Opinion of the International Searching Authority for International Application No. PCT/SG2014/000009, "Fluorescent Cell Cycle Probe Having M-Phase Specificity", date of mailing: Feb. 7, 2014.
Notification Concerning Transmittal of Copy of International Preliminary Report on Patentability for International Application No. PCT/SG2014/000009, "Fluorescent Cell Cycle Probe Having M-Phase Specificity", date of mailing: Jul. 23, 2015.

* cited by examiner

*Primary Examiner* — Paul A Zucker
(74) *Attorney, Agent, or Firm* — Hamilton, Brook, Smith & Reynolds, P.C.

(57) ABSTRACT

The present invention is directed to a novel family of fluorophores based on the BODIPY scaffold, and methods for their synthesis. The BODIPY-based fluorophores disclosed herein are used for the selective visualization of cells that exist in the M-phase of the cell cycle. The present invention further relates to methods for the image-based monitoring of mitotic progression in live cells.

13 Claims, 10 Drawing Sheets

FLUORESCENT CELL CYCLE PROBE HAVING M-PHASE SPECIFICITY

RELATED APPLICATIONS

This application is the U.S. National Stage of International Application No. PCT/SG2014/000009, filed on Jan. 14, 2014, which designates the U.S., published in English, and claims the benefit of U.S. Provisional Application No. 61/752,125, filed on Jan. 14, 2013. The entire teachings of the above applications are incorporated herein by reference.

BACKGROUND OF THE INVENTION

The cell cycle is a vital process in which a parent cell divides into two or more daughter cells. In general, the cell cycle progression consists of four distinct phases: G1 phase, S phase, G2 phase, and mitosis. The mitosis is a part of the full life cycle of a cell in actively proliferating cells, resulting in the division of duplicated sets of chromosomes and two genetically identical daughter cells. Although mitosis phase is the shortest phase in cell cycle, mitosis orchestrates major changes in multiple cellular components. If the failure of cell cycle occurs, the failure of cell-cycle checkpoint regulations often results in aneuploidy and genetic instability, culminating in cell death or in cancer development. It has recently been suggested that determination of cell proliferation and its distinction from incomplete cell cycle progression is an important element in cell biology and regenerative medicine. However, current methods to monitor cell division in live cells, and to reliably distinguish between acytokinesis and endoreduplication, are limited and complicate determination of cell pool identities.

Therefore, there remains a need to develop methods for monitoring cell division. Similarly, there is a need for the development of a novel class of fluorescent probes useful for monitoring cell proliferation. These probes should be reliable and selective for visualizing cells in the mitosis phase of the cell cycle.

SUMMARY OF THE INVENTION

The present invention is based on the discovery of selective fluorescent probes for the visualization of cells that exist in the M-phase (mitosis phase) of the cell cycle. Accordingly, in one embodiment, the invention is a novel class of BODIPY fluorescence dyes. The present invention also relates to methods of synthesis of the BODIPY fluorescence dyes. The compounds of the present invention are synthesized through combinatorial methods, enabling facile access to a broad class of compounds with two sites of derivatization. In another embodiment, the invention relates to methods for the visualization of cells that exist in the M-phase of the cell cycle. The BODIPY fluorescence dyes disclosed herein are also used in the image-based monitoring of mitotic progression in live cells.

BRIEF DESCRIPTION OF THE DRAWINGS

The foregoing will be apparent from the following more particular description of example embodiments of the invention, as illustrated in the accompanying drawings.

FIG. 3A displays live cell imaging of BDL-F2-stained mitotic cell without Tubulyzine B treatment. FIG. 3B reveals the dynamic distribution of BDL-F2 at different stages of Mitosis in RPE1:H2B:GFP cells. In the first row of FIG. 3B, time lapse imaging shows the BDL-F2 signal at Mitosis progression of RPE1:H2B:GFP cells expressing a H2B-GFP fusion protein after BDL-F2 (0.4 µM) for 3 h. Time lapse imaging was taken every 3 min on an inverted Nikon Ti-fluorescence microscope system using a 10× objective lens with TRITC filter. In the second row of FIG. 3B, time lapse imaging shows fluorescence signaling, viewed with a channel suitable for GFP (Ex/Em. 470-510 nm/515-555 nm) visualization. The merged images are shown in the third row of FIG. 3B.

DETAILED DESCRIPTION OF THE INVENTION

A description of example embodiments of the invention follows.

A novel class of fluorescent probes having a core structure of 4,4-difluoro-4-bora-3a,4a-diaza-s-indacene (BODIPY) is disclosed herein. BODIPY fluorescent dyes are known in the art for outstanding photophysical properties as a fluorescent scaffold, such as high photostability, high fluorescent quantum yield, high extinction coefficient, and narrow emission bandwidth. The class of BODIPY compounds disclosed herein includes a novel cell proliferation probe, BDL-F2. BDL-F2 exhibits a change in fluorescent intensity in response to different stages of cell proliferation.

BODIPY-Derived Fluorescent Probes

In some embodiments of the invention, the BODIPY fluorescent probes have the structure of formula (I) or a pharmaceutically acceptable salt thereof:

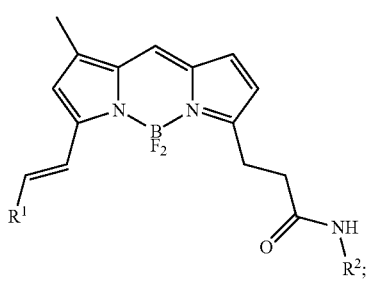

(I)

wherein:

$R^1$ is $(C_6-C_{10})$aryl or $(C_3-C_{12})$heteroaryl, optionally substituted at any position with one or more substituents, each substituent independently selected from $(C_1-C_{10})$alkyl, $—O(C_1-C_6)$alkyl, $(C_2-C_6)$alkenyl, $(C_6-C_{10})$aryl, $—O(C_6-C_{10})$aryl, $—O$(benzyl), $(C_3-C_8)$heteroaryl, halo, hydroxyl, $NR^3R^4$, nitro or $—O(C_2-C_6)$alkenyl, and further wherein each $—O(C_1-C_6)$alkyl, $(C_2-C_6)$alkenyl, $—O(C_6-C_{10})$aryl, $—O$(benzyl) or $(C_3-C_8)$heteroaryl is optionally substituted at any position with one or more substituents, each independently selected from halo, $(C_6-C_{10})$aryl, $(C_1-C_{10})$alkyl or $—O(C_1-C_6)$alkyl;

$R^2$ is $(C_1-C_6)$alkyl or $(C_3-C_8)$cycloalkyl, optionally and independently substituted with one or more substituents selected from $—NR^5R^6$, hydroxyl, halo or $—O(C_1-C_6)$alkyl; and $R^3$, $R^4$, $R^5$, and $R^6$, if present, are each independently selected from H, $(C_1-C_6)$alkyl, $(C_6-C_{10})$aryl, $(C_1-C_6)$hydroxyalkyl, or are taken together to form a $(C_3-C_7)$heterocycle.

In particular embodiments of the invention, the BODIPY fluorescent probes have the structure of formula (I), wherein $R^1$ is $(C_6-C_{10})$aryl, optionally substituted at any position with one or more substituents, each substituent independently selected from $(C_1-C_{10})$alkyl or $—O(C_1-C_6)$alkyl, and $R^2$ is $(C_1-C_6)$alkyl, optionally substituted with one or more substituents, each substituent independently selected from $—NR^5R^6$ or hydroxyl.

In a preferred embodiment of the invention, the BODIPY fluorescent probe is BDL-F2 and has the structure of formula (II) or a pharmaceutically acceptable salt thereof:

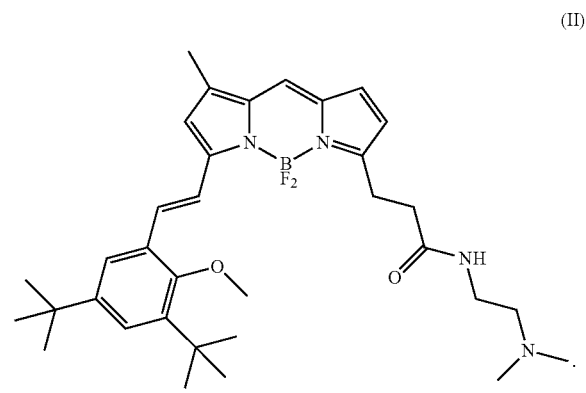

(II)

In another preferred embodiment of the invention, the BODIPY fluorescent probe has the structure of any one of Formulae (IV), (V), (VI), (VII), (VIII), (IX), (X), (XI), or (XII), or a pharmaceutically acceptable salt thereof:

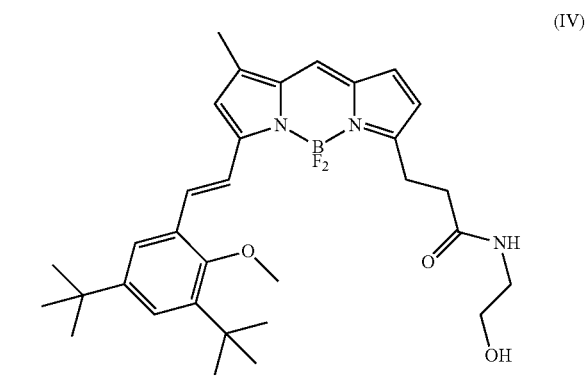

(IV)

-continued
(V)
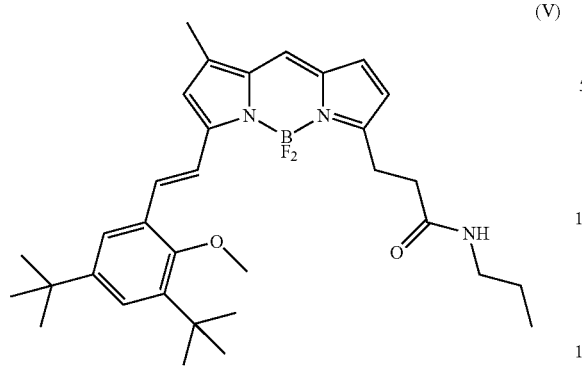
(VI)
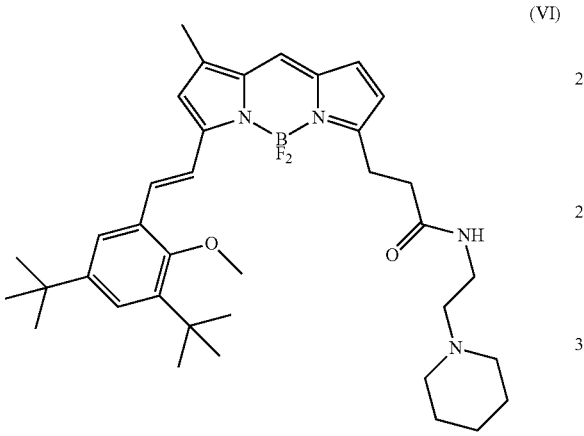
(VII)
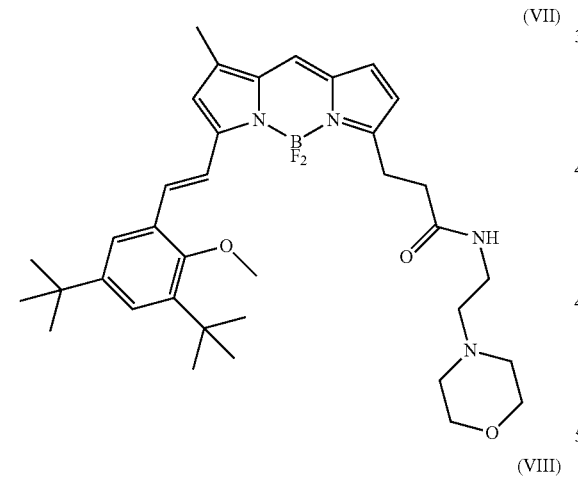
(VIII)
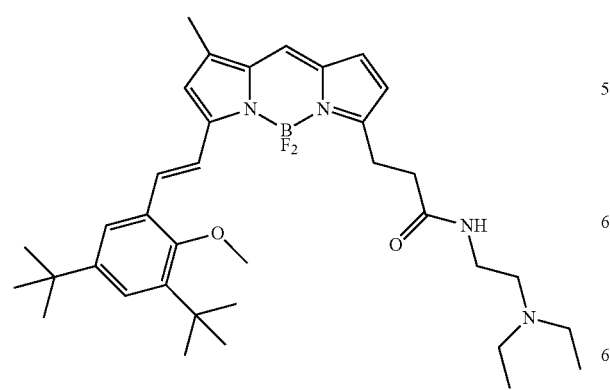
-continued
(IX)
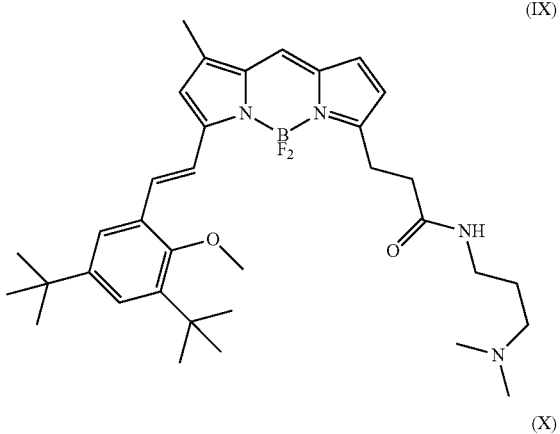
(X)
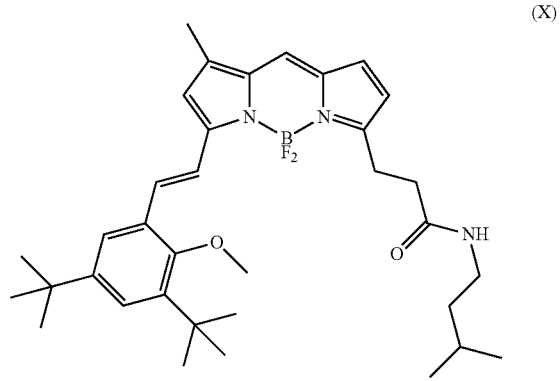
(XI)
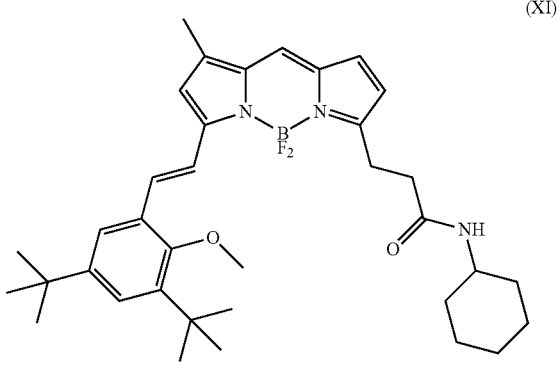
(XII)
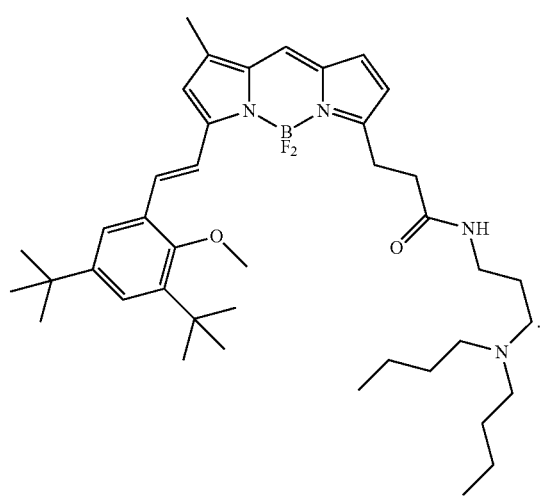

Figure 10:
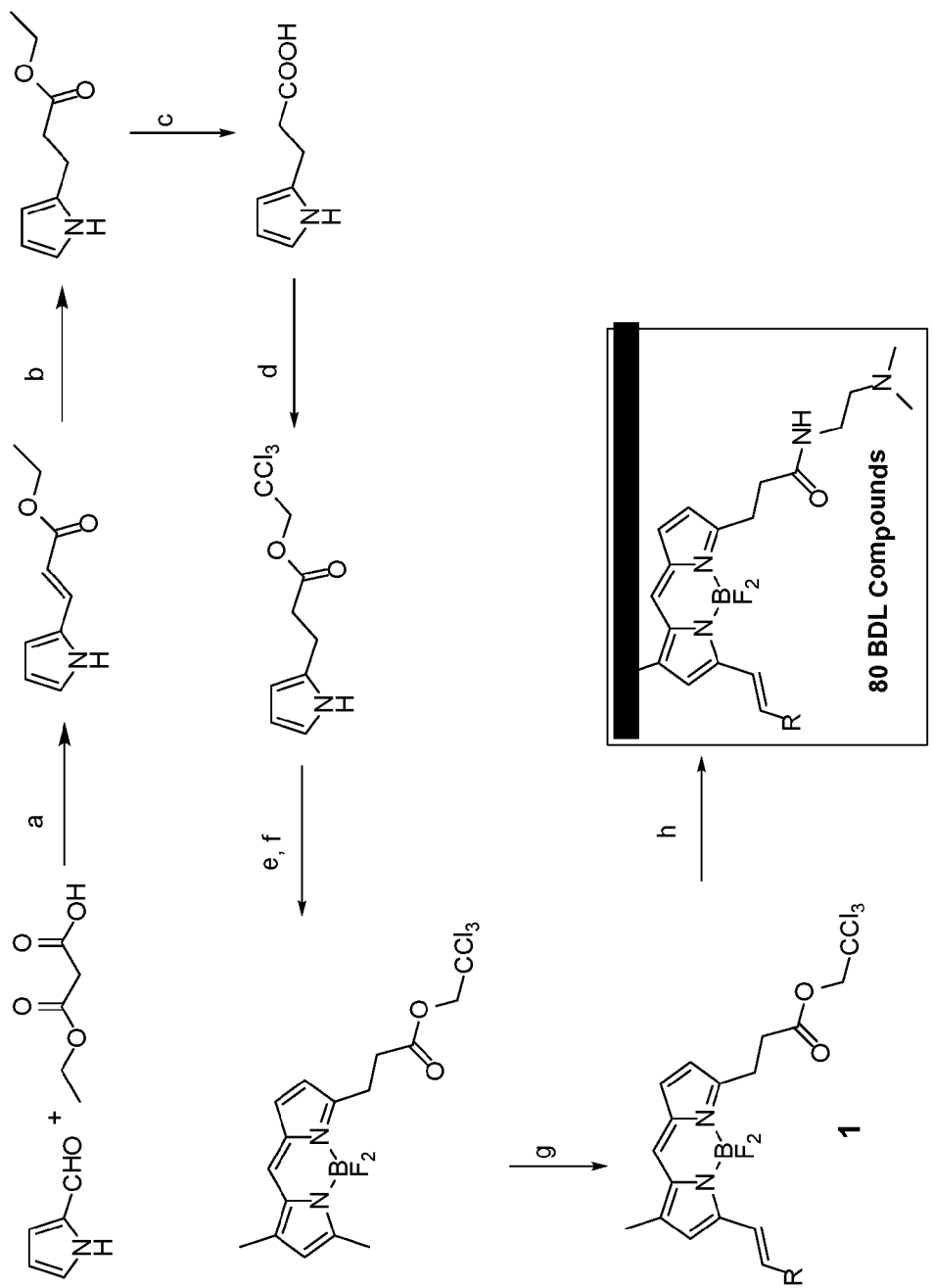
FIG. 10 shows a reaction scheme for the synthesis of a fluorescence BODIPY library (BDL) in which the compounds contain a tertiary amine group.

The present invention further relates to methods for the synthesis of BODIPY fluorescent probes. In an example embodiment, the invention includes methods for the synthesis of a fluorescence BODIPY library (BDL), in which the compounds contain a tertiary amine group. This embodiment is depicted in Scheme 1 as shown in FIG. 10.

Reaction Conditions: (a) pyridine, piperidine, 50° C., 48 h, then 80° C., 24 h; (b) $H_2$, Pd/C, MeOH, RT, 6 h; (c) $K_2CO_3$, $H_2O$/EtOH, reflux, overnight; (d) 2,2,2-trichloroethanol, pyridine, DCC, EA, RT, overnight; (e) 3,5-dimethyl-1H-pyrrole-2-carbaldehyde, $POCl_3$, DCM, RT, 4 h; (f) DIEA, $BF_3OEt_2$, DCM, RT, overnight; (g) R—CHO, pyrrolidine, acetic acid, ACN, 85° C., 15 min; (h) N,N-dimethylethylenediamine, 5 min.

The general synthetic scheme shown in Scheme 1 comprises a step of Knoevenagel-type condensation in step (g), in which the $C_3$-methyl group of a BODIPY derivative reacts with an aldehyde of the formula R—CHO. Aldehydes suitable for the Knoevenagel-type condensation include, but are not limited to, structures shown in Table 1.

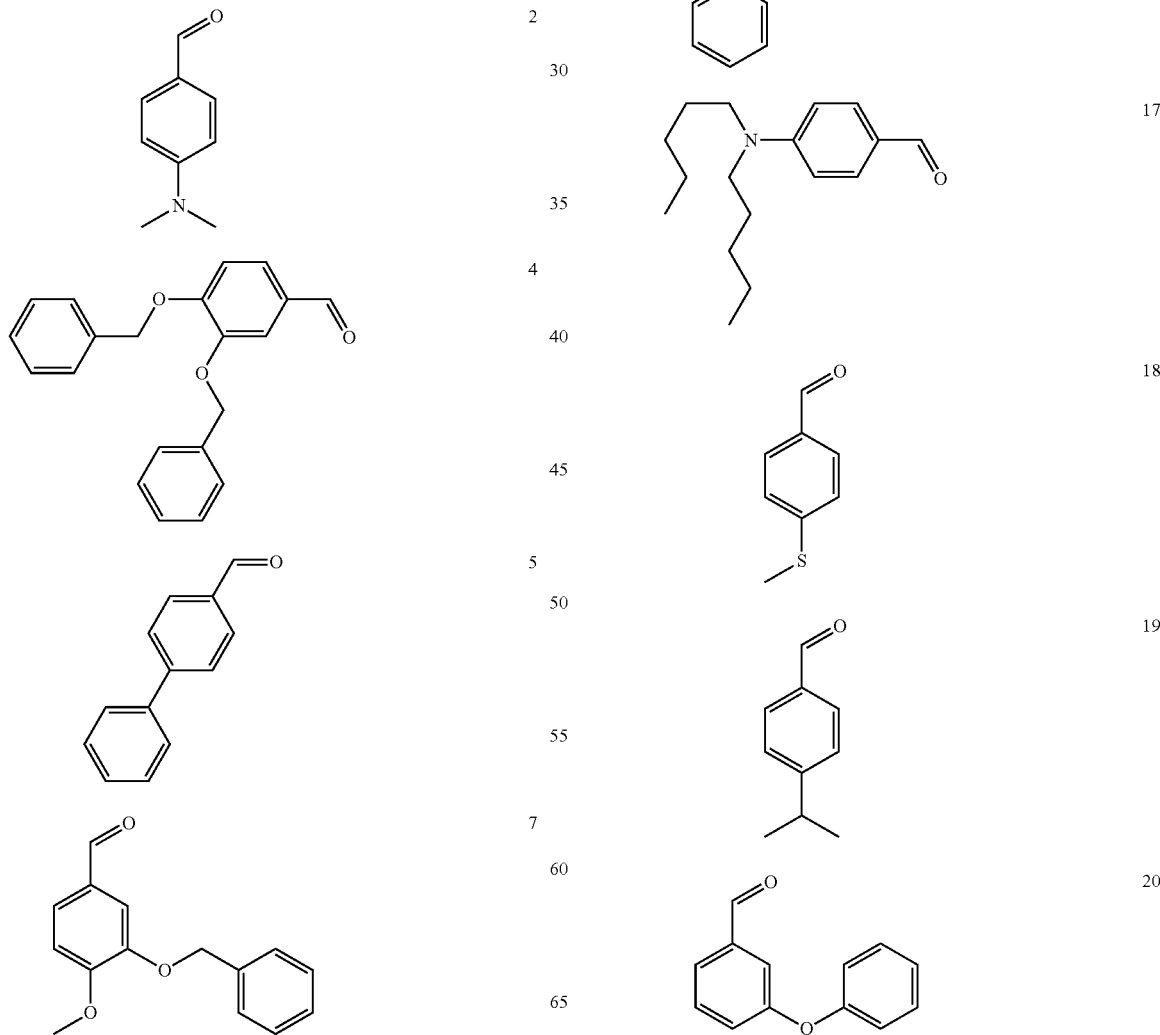

TABLE 1

Aldehyde building blocks employed in the synthesis (R-CHO in Scheme 1).

TABLE 1-continued
Aldehyde building blocks employed in the synthesis (R-CHO in Scheme 1).
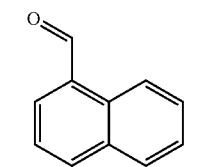 [SMILES: O=Cc1cccc2ccccc12] 25
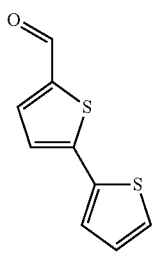 [SMILES: O=Cc1ccc(-c2cccs2)s1] 34
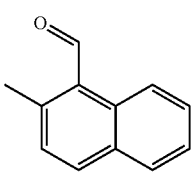 36
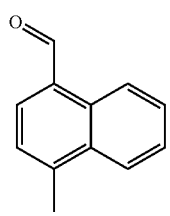 38
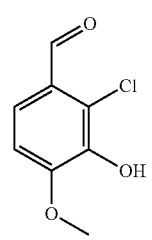 40
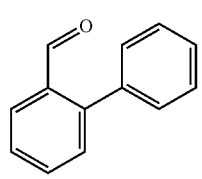 [SMILES: O=Cc1ccccc1-c1ccccc1] 45
TABLE 1-continued
Aldehyde building blocks employed in the synthesis (R-CHO in Scheme 1).
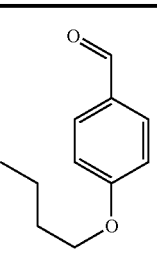 46
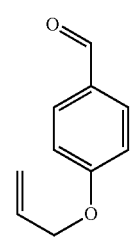 48
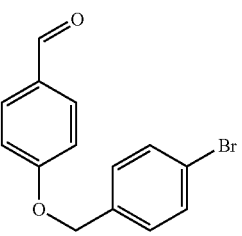 [SMILES: O=Cc1ccc(OCc2ccc(Br)cc2)cc1] 52
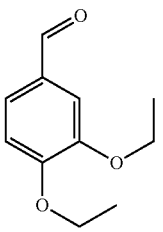 53
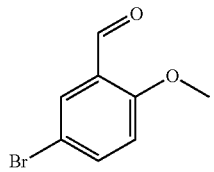 54
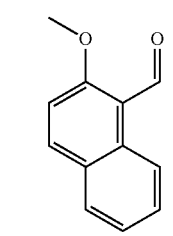 61

TABLE 1-continued
Aldehyde building blocks employed in the synthesis (R-CHO in Scheme 1).
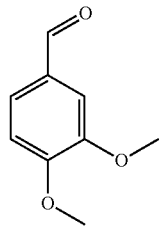 62
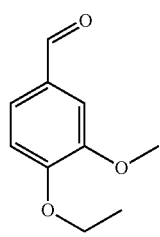 63
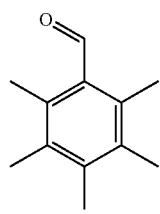 67
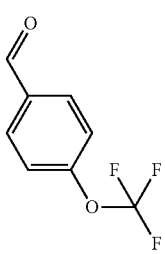 [SMILES: O=Cc1ccc(OC(F)(F)F)cc1] 68
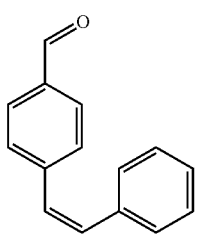 [SMILES: O=Cc1ccc(/C=C\c2ccccc2)cc1] 69
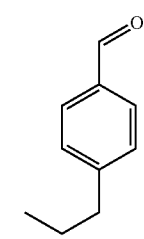 77
TABLE 1-continued
Aldehyde building blocks employed in the synthesis (R-CHO in Scheme 1).
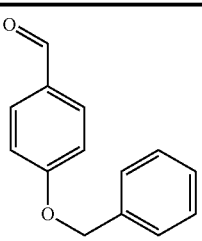 90
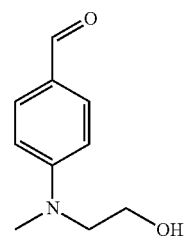 91
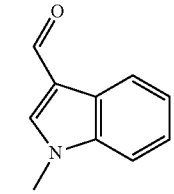 94
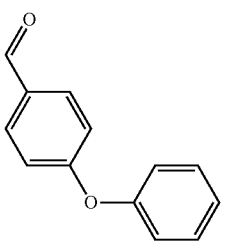 [SMILES: O=Cc1ccc(Oc2ccccc2)cc1] 101
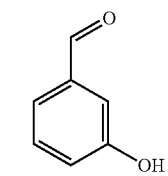 105
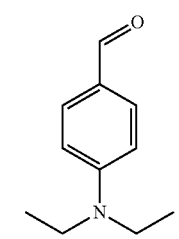 107
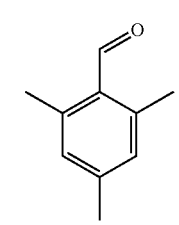 108

TABLE 1-continued
Aldehyde building blocks employed in the synthesis (R-CHO in Scheme 1).
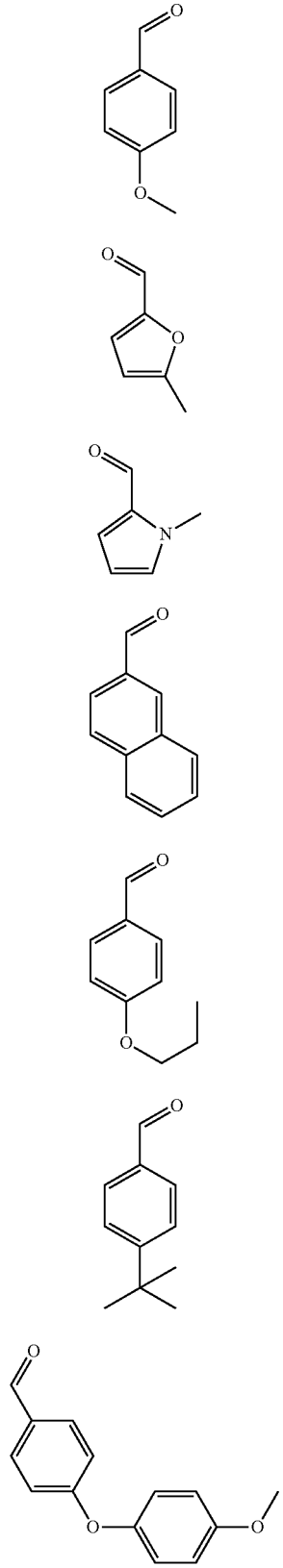
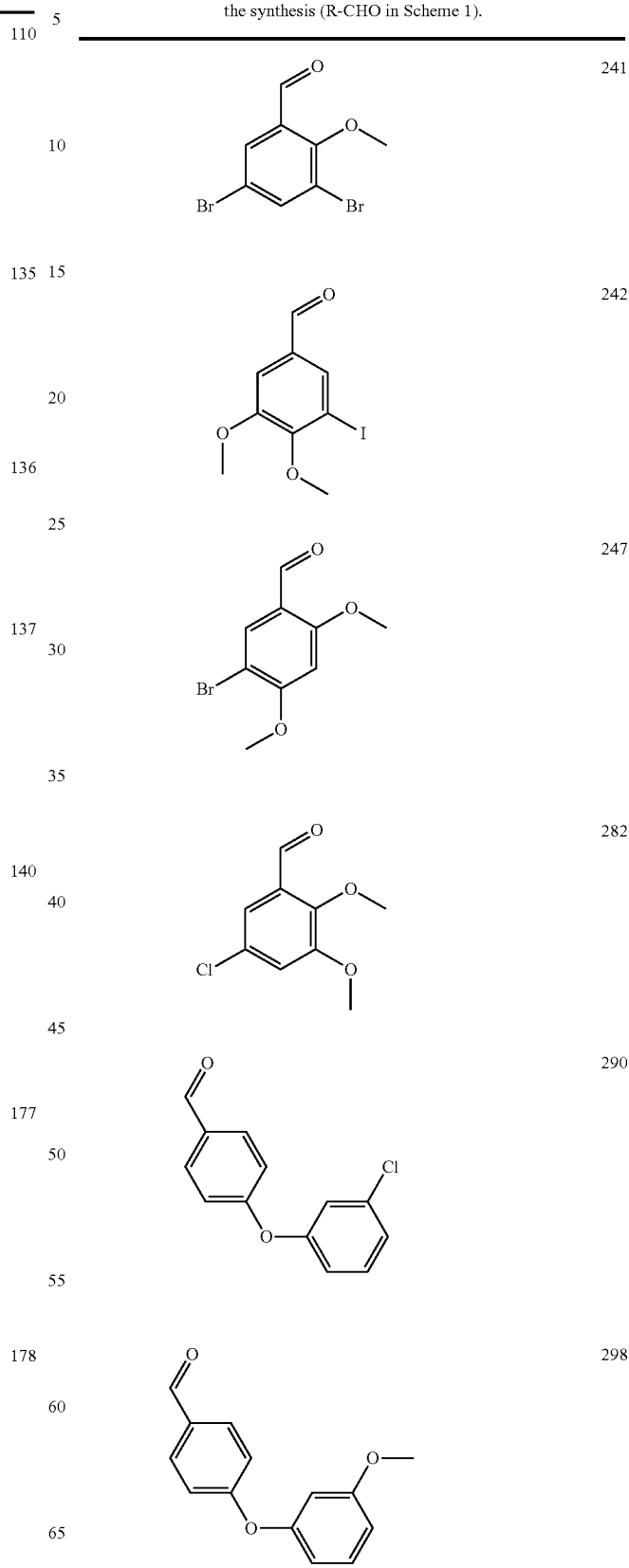

TABLE 1-continued
Aldehyde building blocks employed in the synthesis (R-CHO in Scheme 1).
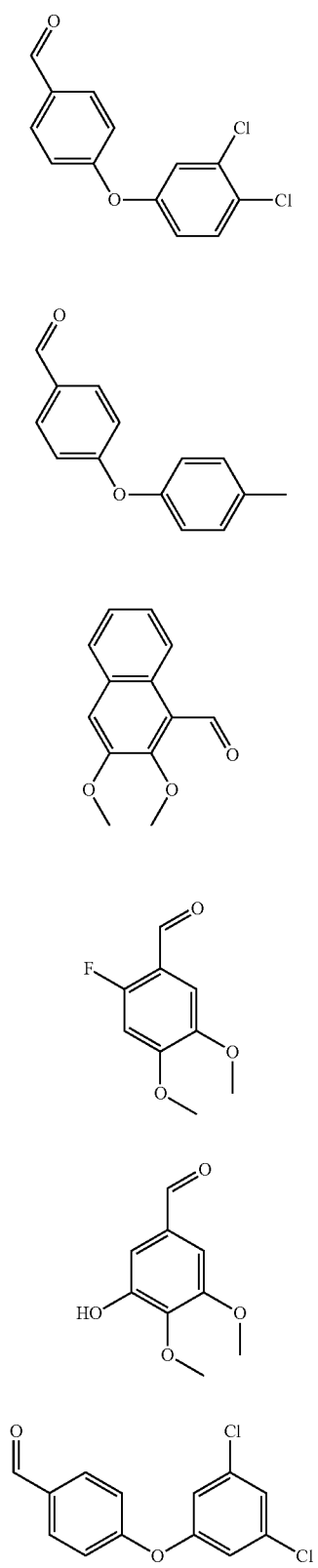
299
300
301
305
307
308
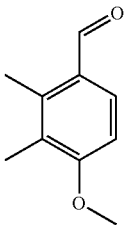 310
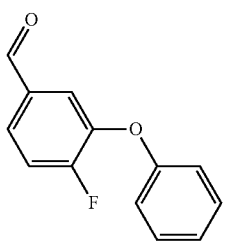 [SMILES: O=Cc1ccc(F)c(Oc2ccccc2)c1] 311
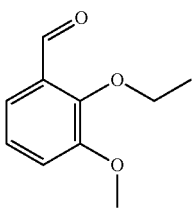 320
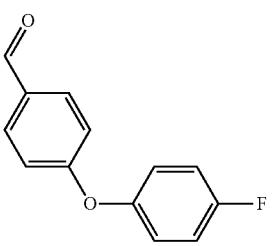 [SMILES: O=Cc1ccc(Oc2ccc(F)cc2)cc1] 322
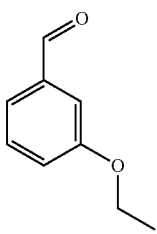 323
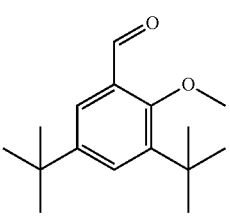 [SMILES: COc1c(C=O)cc(C(C)(C)C)cc1C(C)(C)C] 325

TABLE 1-continued
Aldehyde building blocks employed in
the synthesis (R-CHO in Scheme 1).
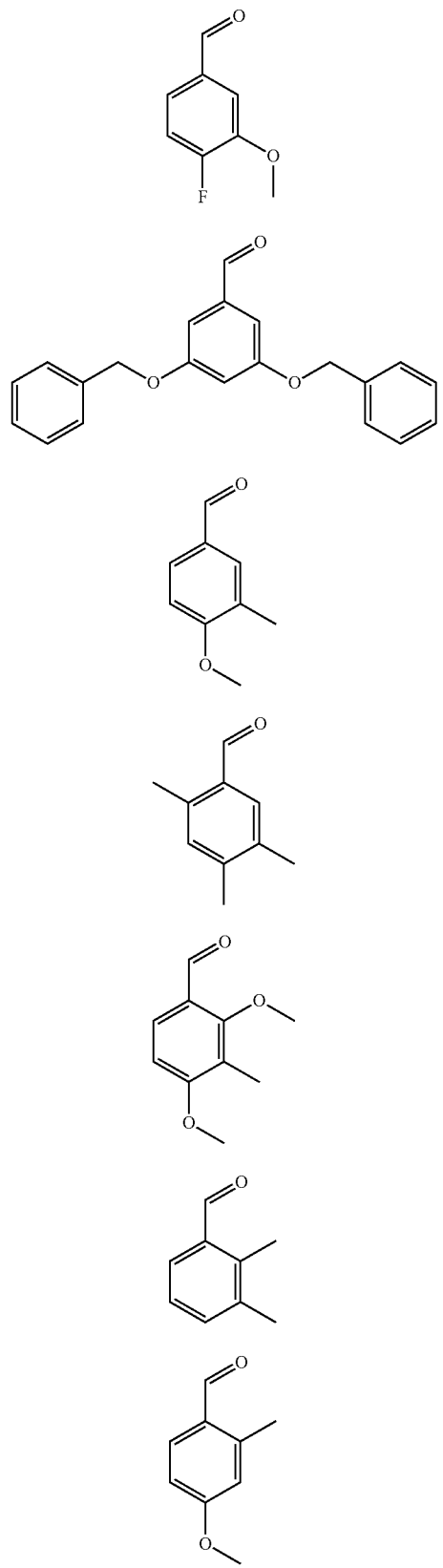
329
331
335
343
347
349
351
TABLE 1-continued
Aldehyde building blocks employed in
the synthesis (R-CHO in Scheme 1).
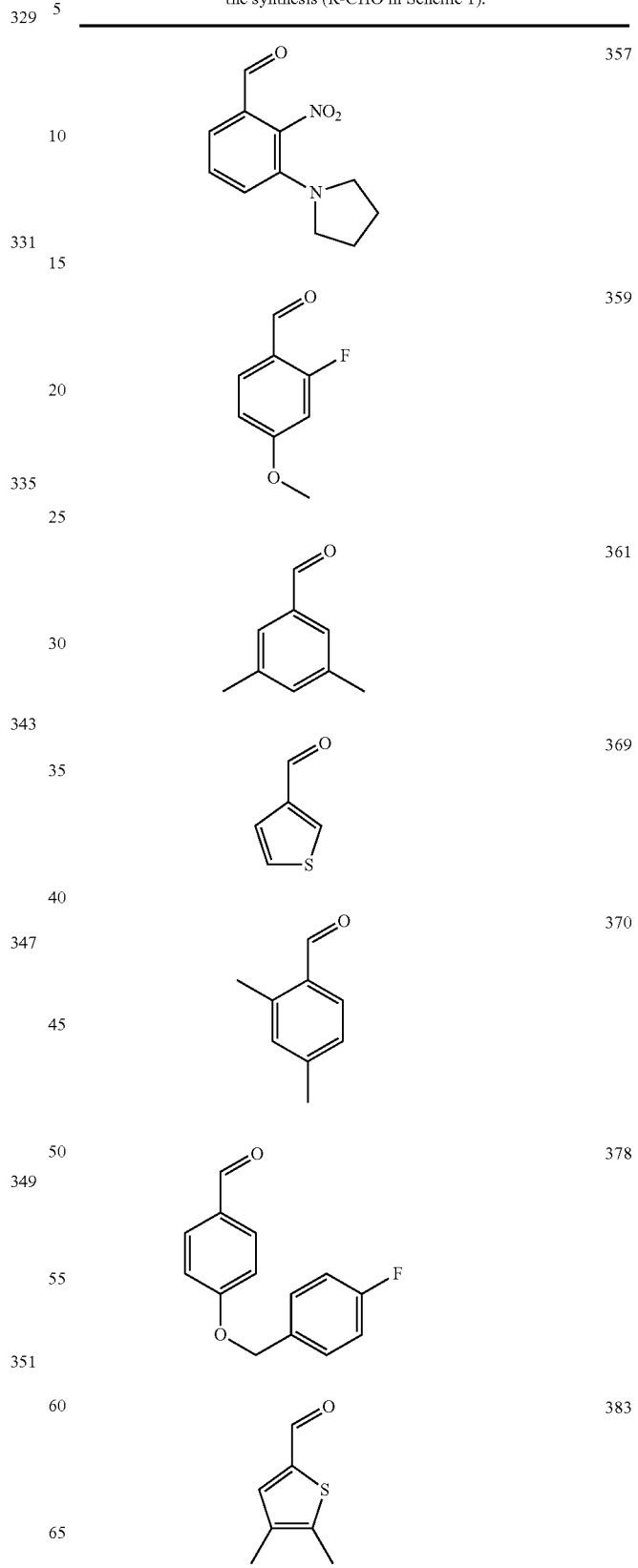
357
359
361
369
370
378
383

TABLE 1-continued

Aldehyde building blocks employed in
the synthesis (R-CHO in Scheme 1).

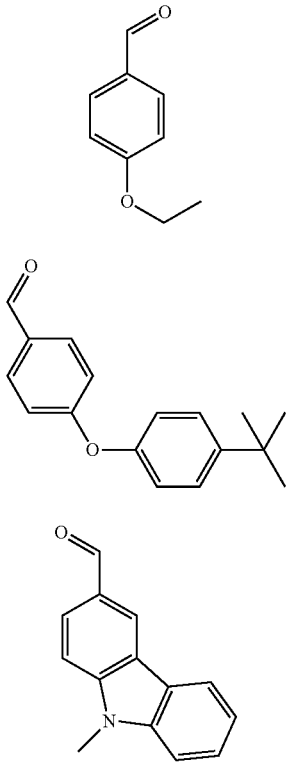

429

435

441

In alternate embodiments of the invention, a compound of Formula (I), or a pharmaceutically acceptable salt thereof, is synthesized by reacting a compound of Formula (III):

(III)

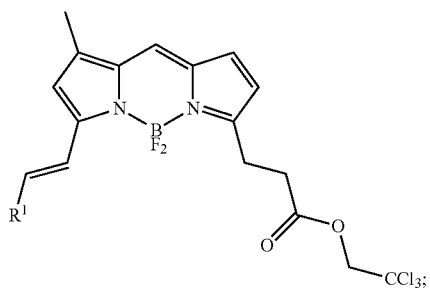

wherein $R^1$ is $(C_6$-$C_{10})$aryl or $(C_3$-$C_{12})$heteroaryl, optionally substituted at any position with one or more substituents, each substituent independently selected from $(C_1$-$C_{10})$alkyl, —O$(C_1$-$C_6)$alkyl, $(C_2$-$C_6)$alkenyl, $(C_6$-$C_{10})$aryl, —O$(C_6$-$C_{10})$aryl, —S$(C_1$-$C_{10})$alkyl, —O(benzyl), $(C_3$-$C_8)$heteroaryl, halo, hydroxyl, $NR^3R^4$, nitro or —O$(C_2$-$C_6)$alkenyl, and further wherein each —O$(C_1$-$C_6)$alkyl, $(C_2$-$C_6)$alkenyl, —O$(C_6$-$C_{10})$aryl, —O(benzyl) or $(C_3$-$C_8)$heteroaryl is optionally substituted at any position with one or more substituents, each independently selected from halo, $(C_6$-$C_{10})$ aryl, $(C_1$-$C_{10})$alkyl or —O$(C_1$-$C_6)$alkyl; and $R^3$ and $R^4$, if present, are each independently selected from H, $(C_1$-$C_6)$alkyl, $(C_6$-$C_{10})$aryl, $(C_1$-$C_6)$hydroxyalkyl, or are taken together to form a $(C_3$-$C_7)$heterocycle;

with a compound having the formula $R^2$—$NH_2$;
wherein $R^2$ is $(C_1$-$C_6)$alkyl or $(C_3$-$C_8)$cycloalkyl, optionally and independently substituted with one or more substituents selected from —$NR^5R^6$, hydroxyl, halo or —O$(C_1$-$C_6)$ alkyl; and $R^5$ and $R^6$, if present, are each independently selected from H, $(C_1$-$C_6)$alkyl, $(C_6$-$C_{10})$aryl, $(C_1$-$C_6)$hydroxyalkyl, or are taken together to form a $(C_3$-$C_7)$heterocycle;

under conditions sufficient to form a compound of Formula (I).

In certain embodiments of the invention, the reaction of a compound of Formula (III) with a compound of the formula $R^2$—$NH_2$ occurs in the absence of solvent and using an excess of primary amine $R^2$—$NH_2$. The reaction time for said reaction is, for example, from about 1 minute to about 10 minutes. Preferably, the reaction time is from about 1 minute to about 5 minutes. In certain embodiments, the reaction is run at room temperature.

In certain embodiments of the invention, the reaction of a compound of Formula (III) with a compound of the formula $R^2$—$NH_2$ yields a compound of the Formula (II). In certain embodiments, the reaction yields a compound of any one of Formulae (IV), (V), (VI), (VII), (VIII), (IX), (X), (XI), or (XII), or a pharmaceutically acceptable salt thereof.

The present invention further relates to methods for assessing the progression of mitosis in a live cell. The method comprises contacting a live cell with a compound of Formula (I) or a pharmaceutically acceptable salt thereof:

(I)

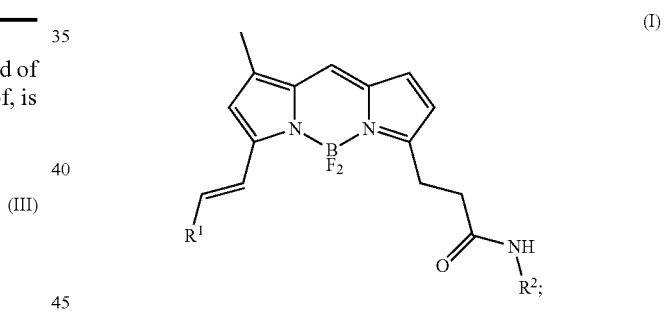

wherein:

$R^1$ is $(C_6$-$C_{10})$aryl or $(C_3$-$C_{12})$heteroaryl, optionally substituted at any position with one or more substituents, each substituent independently selected from $(C_1$-$C_{10})$alkyl, —O$(C_1$-$C_6)$alkyl, $(C_2$-$C_6)$alkenyl, $(C_6$-$C_{10})$aryl, —O$(C_6$-$C_{10})$aryl, —S$(C_1$-$C_{10})$alkyl, —O(benzyl), $(C_3$-$C_8)$heteroaryl, halo, hydroxyl, $NR^3R^4$, nitro or —O$(C_2$-$C_6)$alkenyl, and further wherein each —O$(C_1$-$C_6)$alkyl, $(C_2$-$C_6)$alkenyl, —O$(C_6$-$C_{10})$aryl, —O(benzyl) or $(C_3$-$C_8)$heteroaryl is optionally substituted at any position with one or more substituents, each independently selected from halo, $(C_6$-$C_{10})$ aryl, $(C_1$-$C_{10})$alkyl or —O$(C_1$-$C_6)$alkyl;

$R^2$ is $(C_1$-$C_6)$alkyl or $(C_3$-$C_8)$cycloalkyl, optionally and independently substituted with one or more substituents selected from —$NR^5R^6$, hydroxyl, halo or —O$(C_1$-$C_6)$alkyl; and $R^3$, $R^4$, $R^5$, and $R^6$, if present, are each independently selected from H, $(C_1$-$C_6)$alkyl, $(C_6$-$C_{10})$aryl, $(C_1$-$C_6)$hydroxyalkyl, or are taken together to form a $(C_3$-$C_7)$heterocycle;

to form an incubation media; then incubating the media under conditions sufficient to stain the live cell; and imaging the stained live cell by fluorescence microscopy, in order to assess the progression of mitosis in the live cell.

In certain embodiments of the invention, the progression of mitosis is assessed by collecting fluorescence microscopy data of a stained live cell at at least two discreet time points, and comparing the data sets from the at least two discreet time points. In certain other embodiments, the fluorescence microscopy data is collected continuously. In certain embodiments, a comparison of fluorescence microscopy data provides information about mitosis progression. In an example embodiment, as mitosis progresses, fluorescence data reflects an increase in intensity of a fluorescence signal. For example, an increase in intensity of a fluorescence signal can mean that an M-phase cell exhibits a two-fold increase in fluorescence intensity as compared to a cell that exists outside the M-phase. Alternately, mitosis progression can be assessed by visual observation of a fluorescence image, wherein a cell emits a brighter fluorescence as mitosis progresses. The fluorescence data captured by fluorescence microscopy can be visualized and analyzed, for example, using Nikon NIS elements software. The measurement of fluorescence intensity was determined to be a whole measurement area including, for example, area fraction and mean brightness density variation in interphase cell and mitotic cell using automated measurement function within Nikon NIS elements AR software (vision 4.13).

In certain embodiments of the invention, incubating includes external agitation. In other embodiments of the invention, incubating includes mixing by diffusion. In further embodiments, after treatment with a BODIPY fluorescence dye of Formula (I), cells are incubated in complete medium, comprising DMEM high glucose supplemented with 10% FBS and 1% PS, at about 37° C. for 1 h.

In certain embodiments, imaging includes fluorescence microscopy. In alternate embodiments, imaging includes flow cytometry. Specifically, fluorescence microscopy methods include confocal microscopy, and time-lapse microscopy with live cells.

In preferred embodiments of the invention, the compound of Formula (I) that is used in the method for monitoring mitosis progression is BDL-F2, the compound of Formula (II), or a pharmaceutically acceptable salt thereof:

(II)

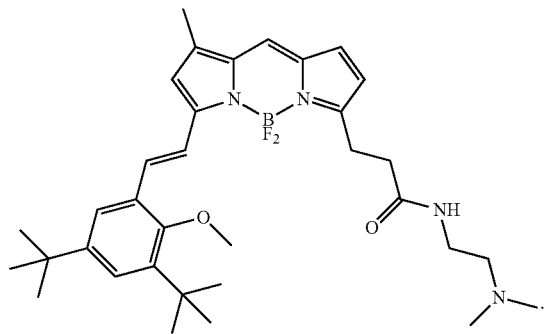

The invention further relates to methods for the preferential staining of an M-phase live cell. These method's comprise contacting a live cell with a compound of Formula (I) or a pharmaceutically acceptable salt thereof:

(I)

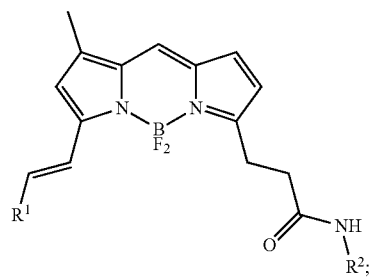

wherein:
$R^1$ is $(C_6-C_{10})$aryl or $(C_3-C_{12})$heteroaryl, optionally substituted at any position with one or more substituents, each substituent independently selected from $(C_1-C_{10})$alkyl, —O$(C_1-C_6)$alkyl, $(C_2-C_6)$alkenyl, $(C_6-C_{10})$aryl, —O$(C_6-C_{10})$aryl, —S$(C_1-C_{10})$alkyl, —O(benzyl), $(C_3-C_8)$heteroaryl, halo, hydroxyl, $NR^3R^4$, nitro or —O$(C_2-C_6)$alkenyl, and further wherein each —O$(C_1-C_6)$alkyl, $(C_2-C_6)$alkenyl, —O$(C_6-C_{10})$aryl, —O(benzyl) or $(C_3-C_8)$heteroaryl is optionally substituted at any position with one or more substituents, each independently selected from halo, $(C_6-C_{10})$aryl, $(C_1-C_{10})$alkyl or —O$(C_1-C_6)$alkyl;

$R^2$ is $(C_1-C_6)$alkyl or $(C_3-C_8)$cycloalkyl, optionally and independently substituted with one or more substituents selected from —$NR^5R^6$, hydroxyl, halo or —O$(C_1-C_6)$alkyl; and $R^3, R^4, R^5,$ and $R^6$, if present, are each independently selected from H, $(C_1-C_6)$alkyl, $(C_6-C_{10})$aryl, $(C_1-C_6)$hydroxyalkyl, or are taken together to form a $(C_3-C_7)$heterocycle;

to form an incubation media; then incubating the media under conditions sufficient to stain the M-phase live cell; and visualizing the stained M-phase live cell by fluorescence microscopy, wherein a live cell that exists within the M-phase is preferentially stained with higher intensity that a live cell that exists in any other phase of the cell cycle.

In certain embodiments, visualizing the stained M-phase live cell includes fluorescence microscopy. In alternate embodiments, visualizing includes flow cytometry. Specifically, fluorescence microscopy methods include confocal microscopy, and time-lapse microscopy with live cells.

In preferred embodiments of the invention, the compound of Formula (I) that is used in the method for preferentially staining an M-phase live cell is BDL-F2, the compound of Formula (II), or a pharmaceutically acceptable salt thereof:

(II)

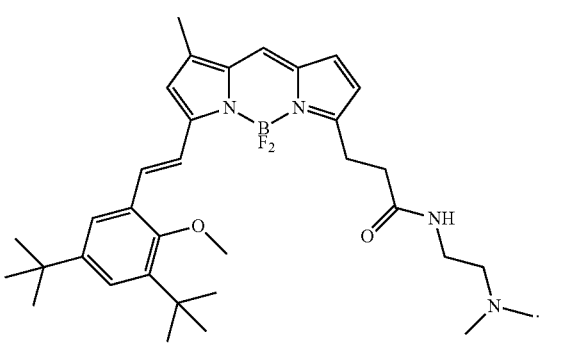

In certain embodiments, the BODIPY compounds of Formula (I) can be used with other fluorescent dyes or stains. In particular embodiments, BDL-F2 is used in conjunction with other fluorescent dyes or stains. Preferably, the excitation and emission window are exclusive. For example, BDL-F2 (excitation 570 nm; emission 585 nm) may be used in conjunction with green fluorescent protein (GFP) (excitation 395 nm; emission 509 nm). Thus, BDL-F2 can be co-stained with either DAPI (Em. 435-485 nm) or FITC (Em. 515-555 nm) or Cy5 (Em. 660-740 nm) channel probes together. If BDL-F2 is used alone, the fluorescence signal exclusively appears in emission window of 605/55 nm (TRITC filter set). Other filter sets DAPI, FITC and Cy5 remain unaffected by the use of BDL-F2 probe, indicating that there is not cross over signal with other filter set windows.

BDL-F2 stained mitotic cells display high fluorescence as compared to interphase cells. Without being bound to theory, data suggests that BDL-F2 is localized to cytoplasm of mitotic cells, and that a cellular component related to staining is in present in high levels in M-phase cells.

DEFINITIONS

All definitions of substituents set forth below are further applicable to the use of the term in conjunction with another substituent.

"Alkyl" as used alone or as part of a larger moiety as in "arylalkyl" or "aryloxyalkyl" means a saturated aliphatic branched or straight-chain monovalent hydrocarbon radicals, typically $C_1$-$C_{10}$, preferably $C_1$-$C_6$. Thus, "($C_1$-$C_6$) alkyl" means a radical having from 1-6 carbon atoms in a linear or branched arrangement. "($C_1$-$C_6$)alkyl" includes methyl, ethyl, propyl, iso-propyl, butyl, iso-butyl, sec-butyl, tert-butyl, pentyl and hexyl.

"Alkylene" means a saturated aliphatic straight-chain divalent hydrocarbon radical. Thus, "($C_1$-$C_6$)alkylene" means a divalent saturated aliphatic radical having from 1-6 carbon atoms in a linear arrangement. "($C_1$-$C_6$)alkylene" includes methylene, ethylene, propylene, butylene, pentylene and hexylene.

"Heterocycle" means a saturated or partially unsaturated monocyclic heterocyclic ring containing one nitrogen atom and optionally 1 additional heteroatom independently selected from N, O or S in addition to carbon atoms. A heterocycle preferably has from 3 carbon atoms to 7 carbon atoms in the heterocycle. When one heteroatom is S, it can be optionally mono- or di-oxygenated (i.e., —S(O)— or —S(O)$_2$—). Examples of monocyclic heterocycle include, but not limited to, azetidine, pyrrolidine, piperidine, piperazine, hexahydropyrimidine, tetrahydrofuran, tetrahydropyran, morpholine, thiomorpholine, thiomorpholine 1,1-dioxide, tetrahydro-2H-1,2-thiazine, tetrahydro-2H-1,2-thiazine 1,1-dioxide, isothiazolidine, or isothiazolidine 1,1-dioxide.

"Cycloalkyl" means saturated aliphatic cyclic hydrocarbon ring. Thus, "$C_3$-$C_8$ cycloalkyl" means (3-8 membered) saturated aliphatic cyclic hydrocarbon ring. $C_3$-$C_8$ cycloalkyl includes, but is not limited to cyclopropyl, cyclobutyl, cyclopentyl, cyclohexyl, cycloheptyl, and cyclooctyl. Preferably, cycloalkyl is $C_3$-$C_6$ cycloalkyl.

The term "alkoxy" is alternately expressed as O-alkyl. Specifically, —O-alkyl connects to the remainder of a molecule through its oxygen atom. In certain embodiments, alkoxy is —O($C_1$-$C_6$)alkyl. "Arylalkoxy" means an alkoxy group substituted at any carbon by an aryl group; "hydroxyalkyl" means alkyl substituted at any position with hydroxy; "aralkyl" means alkyl substituted with an aryl group; "alkoxyalkyl" mean alkyl substituted with an alkoxy group; "alkylamine" means amine substituted with an alkyl group; "cycloalkylalkyl" means alkyl substituted with cycloalkyl; "dialkylamine" means amine substituted with two alkyl groups; "alkylcarbonyl" means —C(O)-A*, wherein A* is alkyl; "alkoxycarbonyl" means —C(O)—OA*, wherein A* is alkyl; and where alkyl is as defined above. Alkoxy is preferably O($C_1$-$C_6$)alkyl and includes methoxy, ethoxy, propoxy, butoxy, pentoxy and hexoxy.

"Cycloalkoxy" means an —O-cycloalkyl group wherein the cycloalkyl is as defined above. Exemplary ($C_3$-$C_7$)cycloalkyloxy groups include cyclopropoxy, cyclobutoxy, cyclopentoxy, cyclohexoxy and cycloheptoxy.

"Hetero" refers to the replacement of at least one carbon atom member in a ring system with at least one heteroatom selected from N, S, and O. A hetero ring system may have 1 or 2 carbon atom members replaced by a heteroatom.

"Halogen" and "halo" are interchangeably used herein and each refers to fluorine, chlorine, bromine, or iodine.

"Cyano" means —C≡N.

"Nitro" means —NO$_2$.

As used herein, an amino group may be a primary (—NH$_2$), secondary (—NHR$_x$), or tertiary (—NR$_x$R$_y$), wherein R$_x$ and R$_y$ are independently any alkyl, aryl, heterocyclyl, cycloalkyl or alkenylene, each optionally and independently substituted with one or more substituents described above, including hydroxyl. The R$_x$ and R$_y$ substituents may be taken together to form a "ring", wherein the "ring", as used herein, is cyclic amino groups such as piperidine and pyrrolidine, and may include heteroatoms such as oxygen, for example as in morpholine.

The terms "haloalkyl", "halocycloalkyl" and "haloalkoxy" mean alkyl, cycloalkyl, or alkoxy, as the case may be, substituted with one or more halogen atoms. The term "halogen" means F, Cl, Br or I. Preferably the halogen in a haloalkyl or haloalkoxy is F.

The term "acyl group" means —C(O)B*, wherein B* is an optionally substituted alkyl group or aryl group (e.g., optionally substituted phenyl).

An "alkylene group" is represented by [CH$_2$]$_z$—, wherein z is a positive integer, preferably from one to eight, more preferably from one to four.

An "alkenylene group" is an alkylene in which at least a pair of adjacent methylenes are replaced with —CH═CH—.

The term "($C_6$-$C_{10}$)aryl" used alone or as part of a larger moiety as in "arylalkyl", "arylalkoxy", "aryloxy", or "aryloxyalkyl", means carbocyclic aromatic rings. The term "carbocyclic aromatic group" may be used interchangeably with the terms "aryl", "aryl ring" "carbocyclic aromatic ring", "aryl group" and "carbocyclic aromatic group". An aryl group typically has 6-10 ring atoms. A "substituted aryl group" is substituted at any one or more substitutable ring atom. The term "$C_6$-$C_{10}$ aryl" as used herein means a monocyclic, bicyclic or tricyclic carbocyclic ring system containing from 6 to 10 carbon atoms and includes phenyl (Ph), naphthyl, anthracenyl, 1,2-dihydronaphthyl, 1,2,3,4-tetrahydronaphthyl, fluorenyl, indanyl, indenyl and the like. The ($C_6$-$C_{10}$)aryl($C_1$-$C_6$)alkyl group connects to the rest of the molecule through the ($C_1$-$C_6$)alkyl portion of the ($C_6$-$C_{10}$) aryl($C_1$-$C_6$)alkyl group. Similarly, the ($C_6$-$C_{10}$)aryl($C_2$-$C_6$) alkenyl group connects to the rest of the molecule through the ($C_2$-$C_6$)alkenyl portion of the ($C_6$-$C_{10}$)aryl($C_2$-$C_6$)alkenyl group The term benzyl (Bn) refers to CH$_2$Ph.

The term "heteroaryl", "heteroaromatic", "heteroaryl ring", "heteroaryl group" and "heteroaromatic group", used alone or as part of a larger moiety as in "heteroarylalkyl" or "heteroarylalkoxy", refers to aromatic ring groups having five to fourteen total ring atoms selected from carbon and at least one (typically 1-4, more typically 1 or 2) heteroatoms (e.g., oxygen, nitrogen or sulfur). They include monocyclic rings and polycyclic rings in which a monocyclic heteroaromatic ring is fused to one or more other carbocyclic aromatic or heteroaromatic rings. The term "5-14 membered heteroaryl" as used herein means a monocyclic, bicyclic or tricyclic ring system containing one or two aromatic rings and from 5 to 14 total atoms of which, unless otherwise specified, one, two, three, four or five are heteroatoms independently selected from N, NH, N($C_{1-6}$)alkyl, O and S. ($C_3$-$C_{10}$)heteroaryl includes furyl, thiophenyl, pyridinyl, pyrrolyl, imidazolyl, and in preferred embodiments of the invention, heteroaryl is ($C_3$-$C_{10}$)heteroaryl.

The term "2-4 member polycyclyl" is a cyclic compound with 2-4 hydrocarbon loop or ring structures (e.g., benzene rings). The term generally includes all polycyclic aromatic compounds, including the polycyclic aromatic hydrocarbons, the heterocyclic aromatic compounds containing sulfur, nitrogen, oxygen, or another non-carbon atoms, and substituted derivatives of these.

The term "Alkenyl" means a straight or branched hydrocarbon radical having a specified number of carbon atoms and includes at least one double bond. An alkenyl group generally has between 2 and 6 carbon atoms. The ($C_6$-$C_{10}$)aryl($C_2$-$C_6$) alkenyl group connects to the remainder of the molecule through the ($C_2$-$C_6$)alkenyl portion of ($C_6$-$C_{10}$)aryl($C_2$-$C_6$) alkenyl.

Pharmaceutically acceptable salts of the compounds of the present invention are also included. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of the compounds of the present invention containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

A "tissue section" is a portion of tissue suitable for analysis. A tissue section can refer to a single tissue section or a plurality of tissue sections.

As used herein, "spectroscopy" encompasses any method by which matter reacts with radiated energy. This includes, but is in no way limited to, microscopy, fluorescence microscopy, UV/Vis spectrometry, and flow cytometry.

A "live cell" is a living cell culture for in vitro analysis. A live cell can refer to a single cell or a plurality of cells.

"M-phase," as used herein, is the phase of the cell cycle that comprises the combined processes of mitosis and cytokinesis. Mitosis is a process in which a eukaryotic cell separates its chromosomes in its cell nucleus into two identical set in two separate nuclei. Cytokinesis is the division of the nuclei, cytoplasm, organelles and cell membrane into two cells. In certain embodiments, M-phase includes prophase, metaphase, anaphase and telophase phase components of cell division. As used herein, "M-phase cell" refers to a cell that is in the M-phase of the cell cycle.

EXAMPLES

The following examples are provided to illustrate one or more preferred embodiments of the invention, but are not limited embodiments thereof. Numerous variations can be made to the following examples that lie within the scope of the invention.

All the reagents and solvents were purchased from Aldrich, Alfa and Acros organics and used without further purification. Column chromatography was performed on Merck 60 silica gel (230-400 mesh). NMR spectra were recorded on a Bruker Avance 300 NMR spectrometer. Chemical shifts are reported as δ in units of parts per million (ppm) and coupling constants are reported as a J value in Hertz (Hz). Mass of all the compounds was determined by LC-MS of Agilent Technologies with an electrospray ionization source. All, fluorescence assays were performed with a Gemini XS fluorescence plate reader Example 1

Synthesis and Characterization of BDL Compounds

Compound $1^2$ (1 µmol) was dissolved in 10 µl N,N-dimethylethylenediamine and stirred for 5 minutes. The reaction mixture was then diluted with DCM and washed with $NaHCO_3$ aqueous solution for 3 times. The organic layer was collected and dried to render BDL compounds in quantitative yield.

BDL-F2 Characterization. ESI-MS m/z ($C_{22}H_{20}BCl_3F_2N_2O_3$) calculated: 592.4 found: 593.4 (M+H). $^1$H NMR (300 MHz, DMSO-d6): 8.06 (s, 1H), 7.69 (d, J=16.2 Hz, 1H), 7.37 (d, J=16.2 Hz, 1H), 7.16 (s, 1H), 7.12 (d, J=3.9 Hz, 1H), 6.42 (d, J=3.9 Hz, 1H), 5.76 (s, 1H), 3.75 (s, 3H), 3.25 (t, J=7.5 Hz, 2H), 3.17 (t, J=7.5 Hz, 2H), 3.14 (t, J=7.5 Hz, 2H), 2.54 (t, J=7.5 Hz, 2H), 2.37 (s, 3H), 2.32 (s, 6H), 1.40 (s, 9H), 1.32 (s, 9H). $^{13}$C NMR (75.5 MHz, DMSO-d6): 11.1, 28.7, 29.0, 30.8, 31.2, 31.3, 34.3, 35.0, 44.4, 57.5, 62.7, 105.0, 109.1, 110.2, 111.1, 115.3, 116.8, 117.2, 121.1, 124.2, 125.5, 126.5, 129.0, 135.9, 142.0, 145.6, 152.6, 156.5, 174.5.

Figure 4:
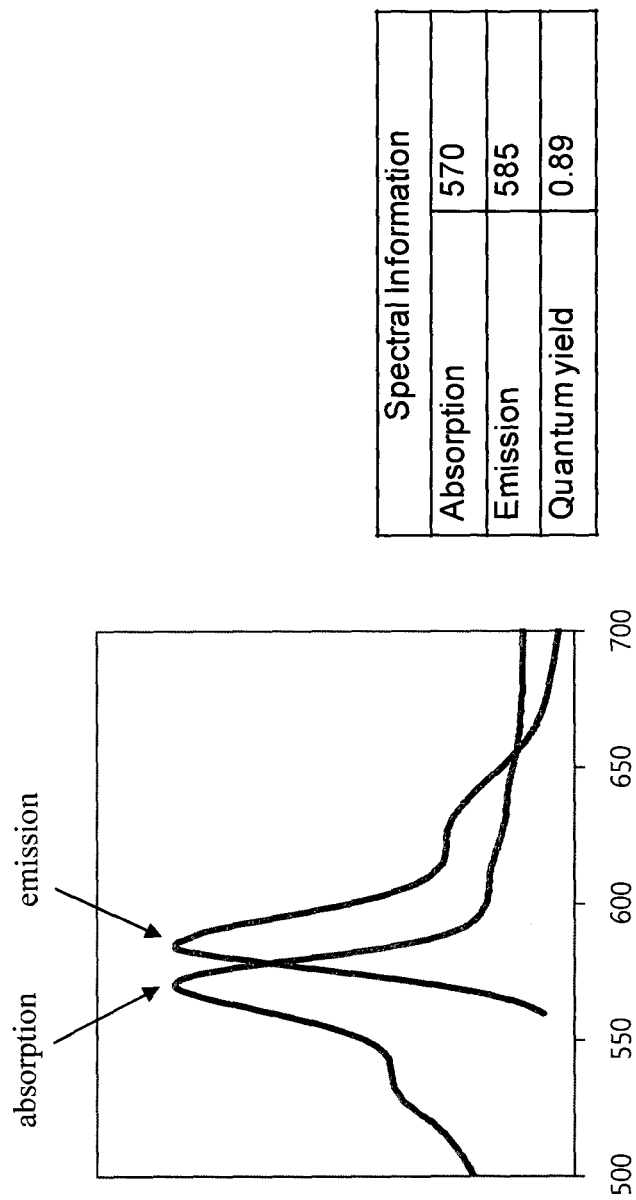
FIG. 4 displays spectroscopic information of BDL-F2.

Fluorescent properties of BDL-F2 are exhibited in FIG. 4. 40 µM solutions in DMSO were prepared and the absorption and emission of each library compound was measured.

Example 2

Cell Culture

RPE1:H2B:GFP (retinal pigmented epithelial cell line stably expressed with histone H2B fused to GFP) cells were cultured on a cell culture dish in Dulbecco's Modified Eagle Medium (life technologies) with 10% FBS and 1% PS. RPE1 cells (hTERT retinal pigmented epithelial cell line_ATCC CRL-4000) were maintained in DMEM F12 1:1 (ATCC 30-2006) supplemented with 10% FBS) with 0.01 mg/ml hygromycin B (Life Technologies).

Example 3

Cell Synchronization

For synchronization of Mitosis, RPE1:H2B:GFP and RPE1 cells were seeded in a plate, synchronized by Tubulyzine B (10 µM) for 24 h. BDL compound-treated cells were stained at 1 µM of Hoechst 33342 from 30 min. The live cell images were taken for an image using ImageXpress Macro™ cellular imaging system with 10× phase contrast objectives at various time points throughout the experiment. All controls in subsequent experiments included 0.1% DMSO. To obtain the live cell imaging, fluorescence microscopy was performed on a Nikon Ti inverted microscope with a CoolSNAP HQ digital camera. A TRITC filter set is a predesigned Nikon Fluorescence Filter Set, available for imaging of green excitation (540/25 nm) and yellow-orange emission (605/55 nm) fluorophores. As shown in FIG. 4, BDL-F2 has the excitation and emission wavelengths 570 nm and 585 nm, respectively, which falls within the spectral range of the TRITC filter set.

Example 4

Cell Cycle Analysis

Mitotic synchronization was induced in RPE:H2B:GFP cells by treatment with Tubulyzine B for 24 h. For FACS analysis with propidium iodide (PI) staining and live condition, cell samples were harvested with trypsinization. To stain the DNA content, cells were fixed with cold 100% methanol and stained with PI at a final concentration of 10 µg/ml. Cell cycle phase distributions were analyzed by flow cytometry (BD Bioscience).

Example 5

Primary Screening Using ImageXpress Macro™ Cellular Imaging System

For primary screening, unsynchronized RPE1:H2B:GFP cells were seeded in 384× well plate, and then treated with Tubulyzine B (10 µM) for 24 h. For each of the 80 BDL compounds, the BDL compound was diluted from 1 mM DMSO stock solutions with the culture medium to make final concentration of 1 µM. The cells were treated with the BDL compound for 1 h. The live cell images were taken using ImageXpress Macro™ cellular imaging system (Molecular Device) with 10× objective lens and the intensity was analyzed by MetaXpress® image processing software (Molecular Device). The hit compound candidates were selected based on the intensity data and manual screening of the raw images. To obtain the live cell imaging, fluorescence microscopy was performed on a Nikon Ti inverted microscope with a CoolSNAP HQ digital camera.

Figure 1:
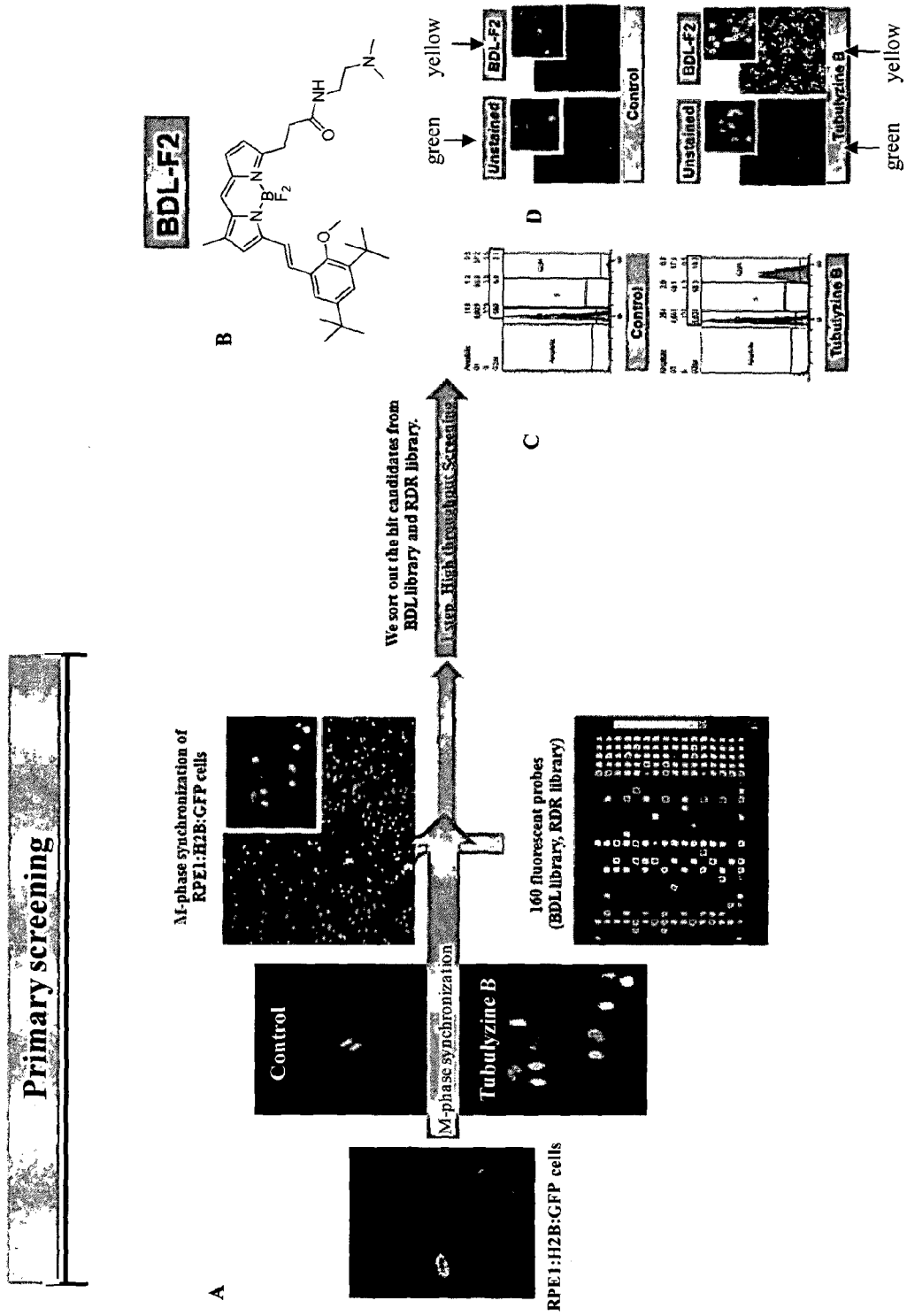
FIG. 1A shows the work flow of primary screening for seeking M-phase probes.
FIG. 1B contains the structure of BDL-F2.
FIG. 1C demonstrates that representative FACS data showed that the cell cycle was arrested at $G_1$ phase (control, DMSO) after DMSO treatment for 24 h. Tubulyzine B-treated RPE1:H2B:GFP cells resulted in a clear accumulation of $G_2$/M phase (bolded box). Upper panel contains control cells; lower panel contains Tubulyzine B-treated cells.
FIG. 1D shows representative live cell imaging from BDL-F2-stained cells, which showed BDL-F2 signal (yellow, TRITC filter) and expression signal of H2B (green, FITC filter) at M-phase (control, Tubulyzine B) after BDL-F2 (1 µM) treatment for 1 h. Upper panel shows the control with BDL-F2; the lower panel shows Tubulyzine B-treated cells with BDL-F2. Live cell imaging of BDL-F2 was carried on an inverted Nikon Eclipse Ti-fluorescence microscopy using a 10× objective lens with TRITC filter. The excitation and emission of BDL-F2 is 570 nm and 585 nm, respectively. H2B:GFP signal was identified as positive selection marker of cell division.

To examine the application of the probe-stained Mitotic cells in live cells, the 80 BDL compounds were screened in control RPE1:H2B:GFP cells and M-phase synchronized RPE1:H2B:GFP cells. RPE1H2P:GFP cells express the histone2B (H2B)-GFP fusion protein in the nucleus. Several studies have revealed that H2B-GFP fusion protein enables sensitive analysis of cell cycle dynamics in living mammalian cells.[3] From the primary screening experiments, five primary hit compounds (BDL-F2, BDL-A3, BDL-A4, BDL-B5 and BDL-C9) were selected from BDL derivative of designated yellow. These compounds stained M-phase brighter than interphase (FIG. 1D).

Example 6

Figure 2:
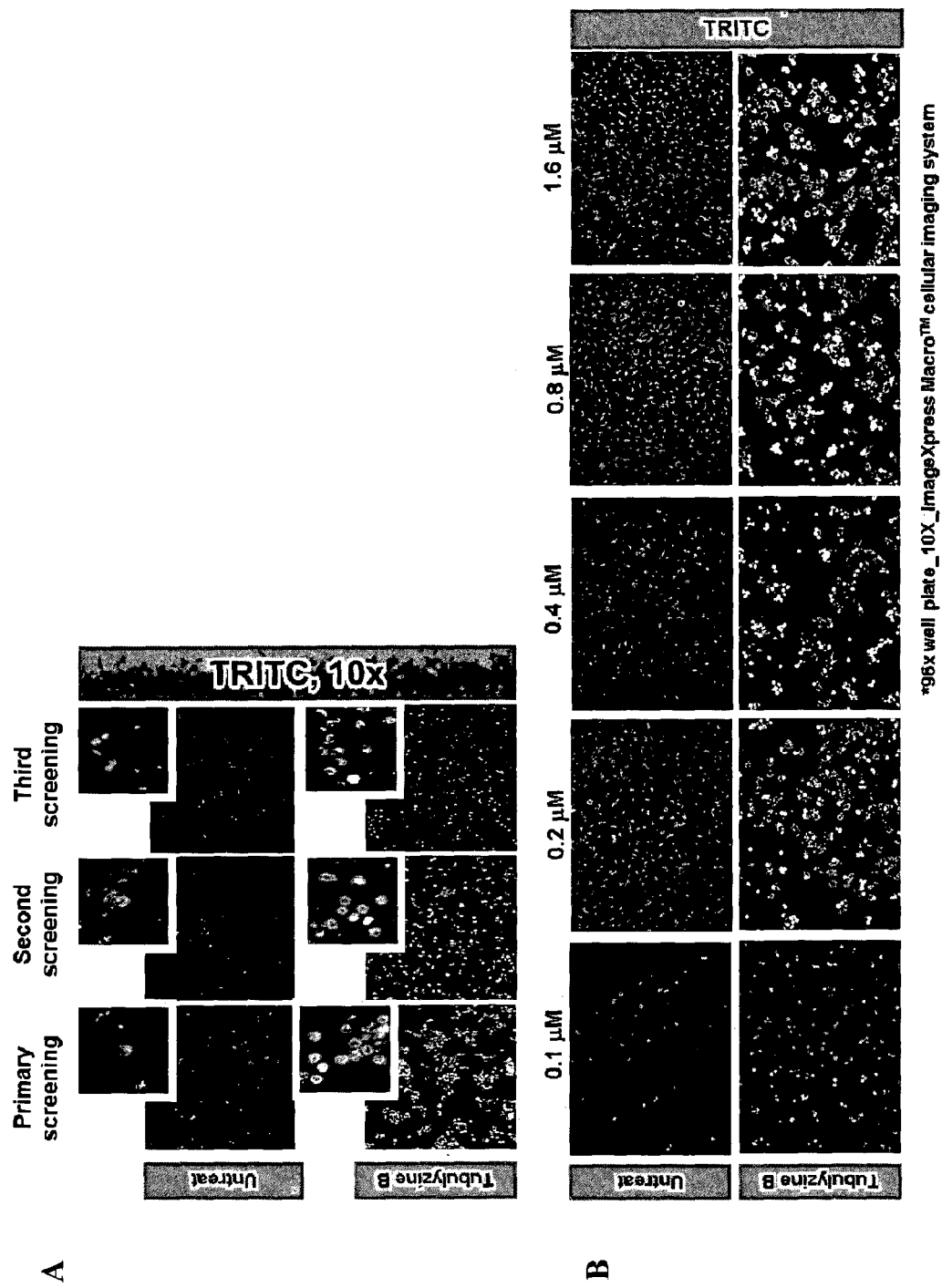
FIG. 2A shows live cell imaging from BDL-F2-stained cells, which exhibited BDL-F2 signal (yellow, TRITC filter) at M-phase (untreated control and Tubulyzine B-treated) after BDL-F2 (1 µM) treatment for 1 h. The upper panel contains control cells with BDL-F2; the lower panel shows Tubulyzine B with BDL-F2. Live cell imaging of BDL-F2 was carried on an inverted Nikon Eclipse Ti-fluorescence microscopy using a 10× objective lens with TRITC filter.
FIG. 2B shows dose-dependent BDL-F2 stained RPE1:H2B:GFP cells. Control and tubulyzine B-treated RPE1:H2B:GFP cells were treated with BDL-F2 (0, 0.2, 0.4, 0.8, 1.6 µM) for 1 h.

Fluorophores for Selective Staining of Mitotic Cells Using ImageXpress Macro™ Cellular Imaging System To confirm the primary screening results, RPE1:H2B:GFP cells and M-phase synchronized RPE1:H2B:GFP cells were each incubated with each of the hit compounds and analyzed in random access with using ImageXpress Macro™ cellular imaging system with 10× phase contrast objectives. These data are representative of at least three independent experiments. FIG. 2A showed that BDL-F2 (FIG. 1B) stained M-phase synchronizing RPE1:H2B:GFP cells stained brightly compared to control cells among the 5 hit compounds. These data are representative of at least three independent experiments. Moreover, BDL-F2 stained the Tubulyzine B induced Mitotic cells in a dose-dependent fashion (FIG. 2B). These data are representative of at least three independent experiments.

Figure 5:
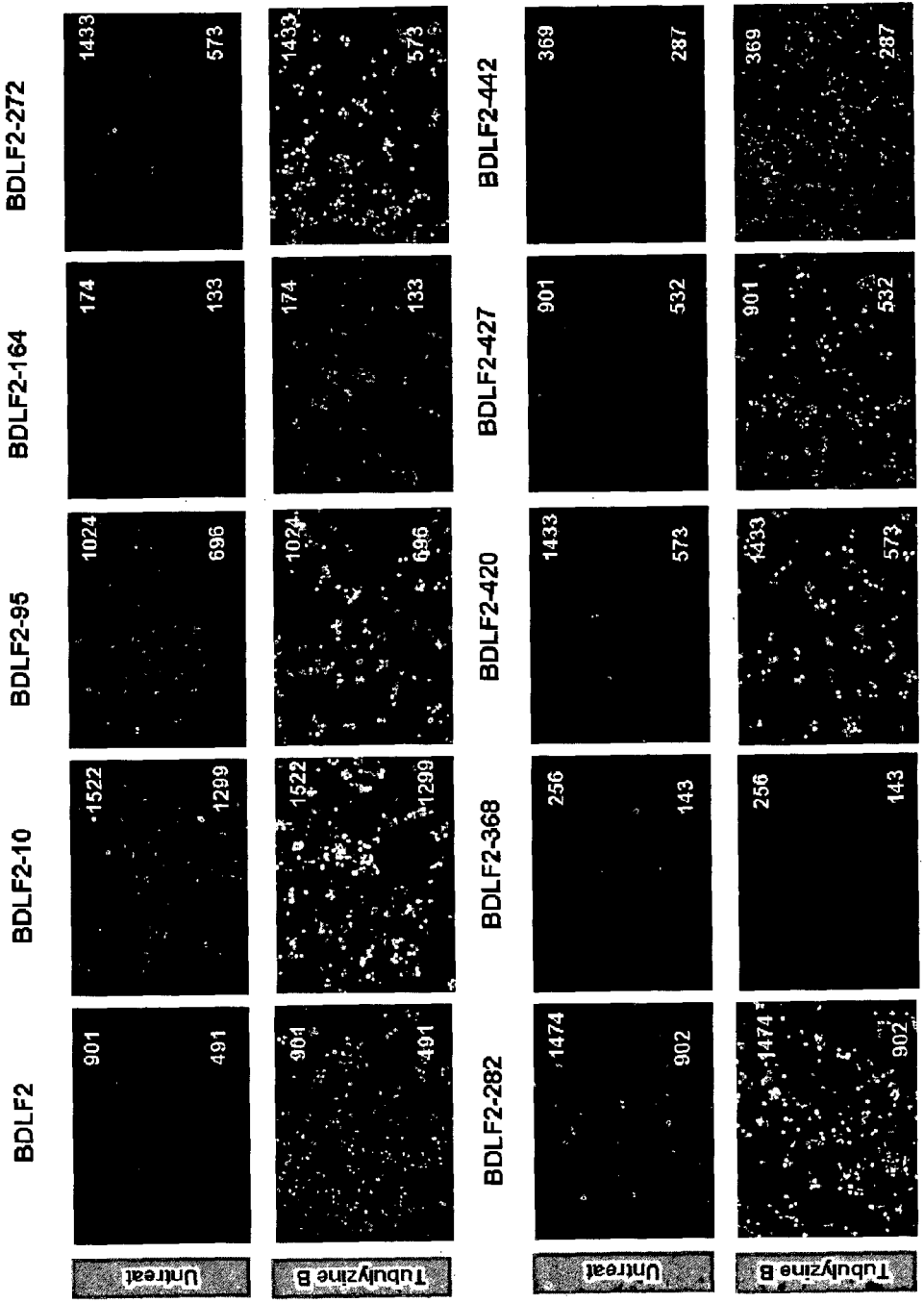
FIG. 5 shows selective staining of M-phase cells by nine BDL-F2 derivative compounds. Representative TRITC image showed the signal of nine BDL-F2 derivative compounds at M-phase (untreated control, and treated with Tubulyzine B) after 1 h treatment with each of the nine BDL-F2 derivative compounds (0.4 µM). The upper panels contain control cells with nine BDL-F2 derivative compounds; the lower panels contain cells treated with Tubulyzine B with nine BDL-F2 derivative compounds. These data are representative of at least three independent experiments.

Moreover, RPE1:H2B:GFP cells and M-phase synchronized RPE1:H2B:GFP cells were incubated with nine BDL-F2 derivative compounds and analyzed in random access with using ImageXpress Macro™ cellular imaging system with 10× phase contrast objectives. FIG. 5 shows that BDL-F2-10 (Formula (IV)), BDL-F2-95 (Formula (V)), BDL-F2-272 (Formula (VI)), BDL-F2-282 (Formula (VII)), BDL-F2-420 (Formula (VIII)), BDL-F2-427 (Formula (IX)), and BDL-F2-442 (Formula (X)) compounds stained M-phase synchronized RPE1:H2B:GFP cells brightly compared to control cells among the nine BDL-F2 derivative compounds.

Example 7

Flow Cytometry and Immunostaining in M-Phase Cells

Flow cytometry was performed on BD FACS LSR II analyzer. Mitotic block was induced in RPE1 cells by treatment with tubulyzine B (10 µM) for 24 h before analysis. Control cells were not treated with tubulyzine B. BDL-F2-stained cells at 1 µM were stained for 1 h. To assess the fluorescence intensity of BDL-F2-stained cells, cells were collected. The fluorescence intensity was then analyzed by flow cytometry (BD Bioscience).

For immunostaining, RPE1 cells were seeded onto coverglass, and then stained with BDL-F2 (1 µM) for 1 h. For immunostaining, coverglass was rinsed for 5 min in PBS, fixed for 15 min in 4% PFA, and incubated for 30 min in 0.5% Triton-X 100 buffer. Phospho-Histone H3 (Ser 10) antibody (Cell signaling) was diluted in dilution buffer (1% BSA in PBS) and incubated overnight at 4 degree. Following three time washes in wash buffer (3% BSA in PBS), a fluorescent conjugated secondary antibody was added, and incubated for 2 h. The coverglass was washed in PBS, and images were taken with Nikon fluorescent microscopy.

Figure 6:
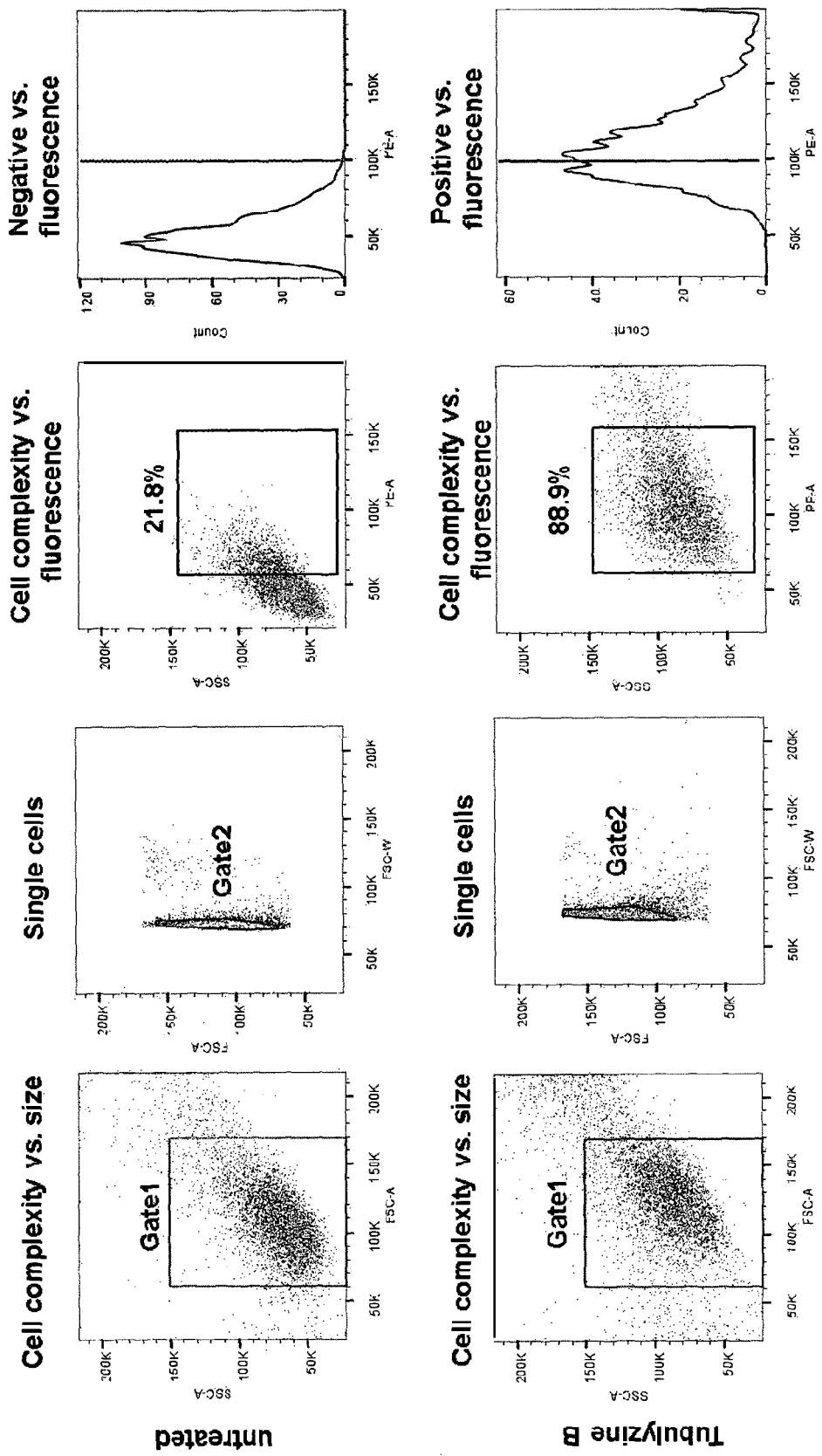
FIG. 6 shows a flow cytometry analysis of BDL-F2 between control (upper panel; not treated with Tubulyzine B) and Tubulyzine B-induced M-phase arrest cells (lower panel). Flow cytometry analyses showed that a large of number of the M-phase arrested cells displayed elevated side scatter signal intensity with high BDL-F2 fluorescence in Tubulyzine B-group, by plotting cell size as measured by forward scattered light.
Figure 7:
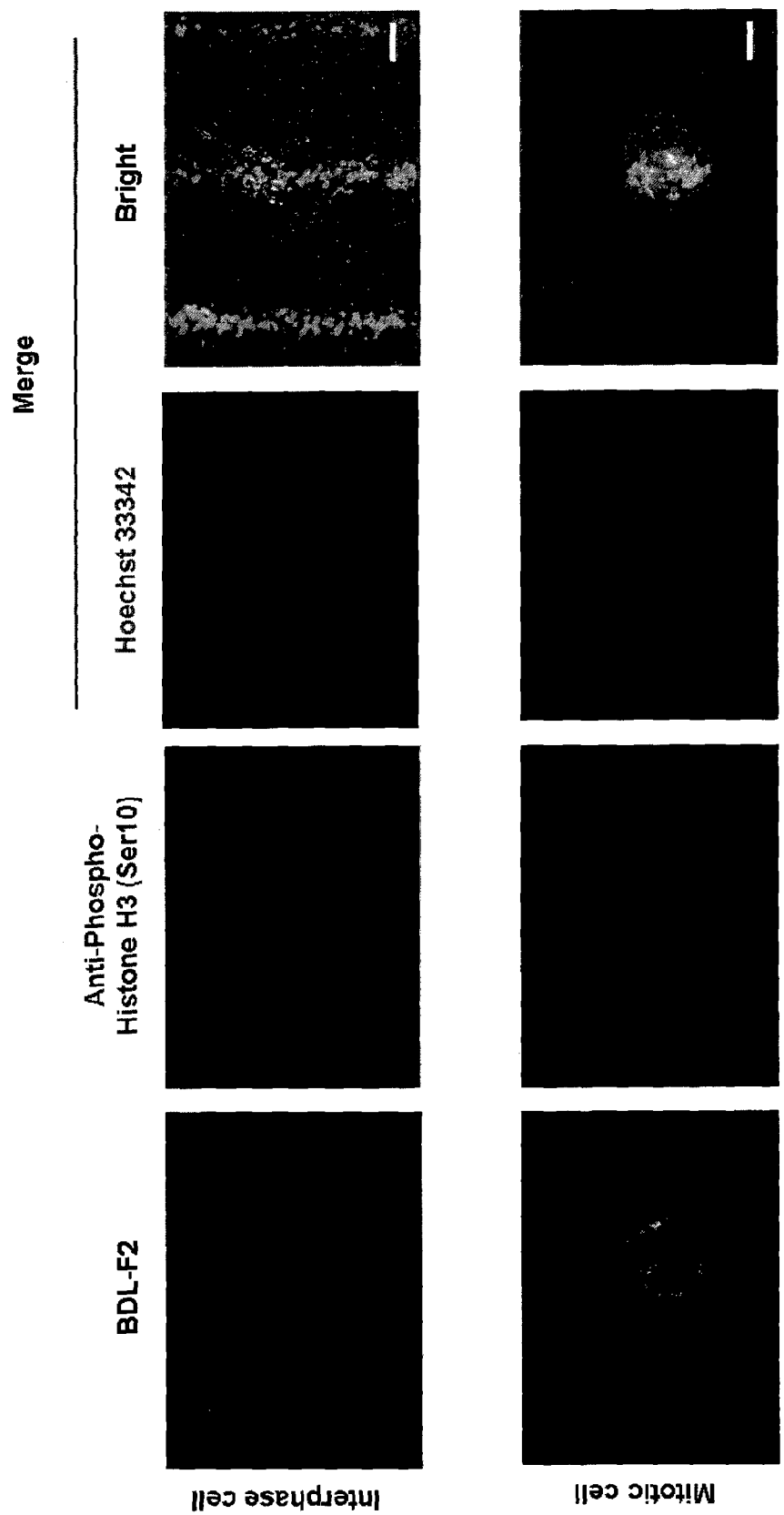
FIG. 7 shows colocalization of BDL-F2 fluorescence and mitotic cells. Increased phosphorylation of histone H3 at Ser10 was observed in mitotic cells (lower panel). Interphase cells were used as control (upper panel). Mitotic cells were generated through M-phase arrest by Tubulyzine B. Phospho- Histone H3 (Ser10) antibody, second column, stains the mitotic cells (lower panel) in red; BDL-F2 stains the mitotic cells a yellow color, and Hoechst 33342 stains a blue color; Size bar, 20 µm; 100×). Immunofluorescent staining of Phospo-Histone H3 (Ser10) antibody showed localization in the same region as the BDL-F2 dye stained with high intensity.

To confirm the selective staining of M-phase cells by BDL-F2, RPE cells and M-phase synchronized RPE1 cells were stained with BDL-F2. After 1 h, the fluorescence intensity was analyzed by flow cytometry and immunostaining with Phospho-Histone H3 (Ser10) antibody. According to flow cytometry analysis, histogram and side scatter plots exhibited a shift in the fluorescence intensity of BDL-F2-stained M-phase arrest group compared to control cells (FIG. 6). Phospho-Histone H3 (Ser10) antibody recognizes Histone H3 only when the Ser10 residue is phosphorylated. Furthermore, it has been reported that phosphorylation at ser10 in the histone H3 tail is an important event for the onset of mitosis.[4] Accordingly, as shown in FIG. 7, Phospho-Histone H3 (Ser10) antibody showed a diffuse staining of chromatin in M-phase arrested cells. Bright fluorescence of BDL-F2 dye was observed in the Phospho-Histone H3 (Ser10) antibody positive cells. Therefore, these data suggest the use of BDL-F2 as a fluorescent dye for identifying and quantifying live mitotic cells through flow cytometry and imaging platforms.

Figure 8:
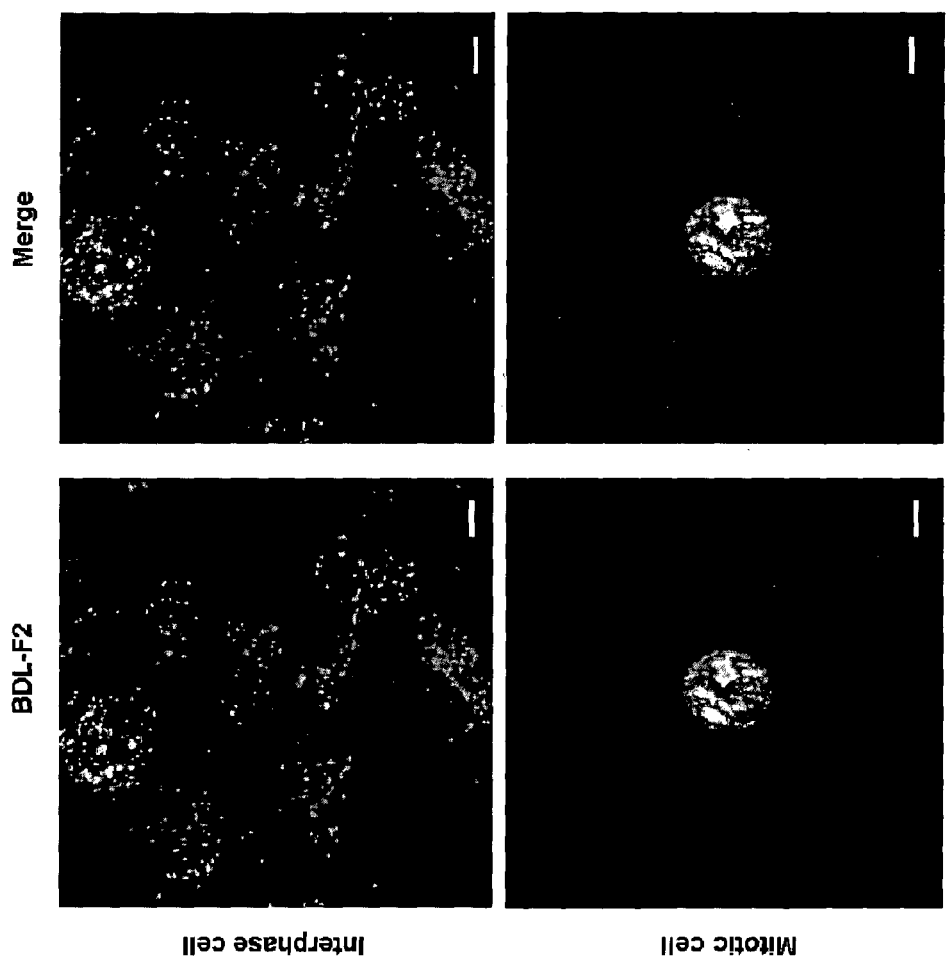
FIG. 8 shows live cell imaging with a nucleic acid stain marker Hoechst 33342 and a fluorescent BDL-F2 dye. Confocal microscopy image showed the distribution of the BDL-F2 dye, resembling the distribution of the cytoplasm, inside the cell. (upper panel: interphase cells, control; lower panel: mitotic cells, Tubulyzine B-induced M-phase arrested cells; BDL-F2 stains a yellow color; Hoechst 33342 stains with a blue color; Size bar, 10 µm; 100×).

In order to precisely identify the localization of BDL-F2 in live cell, live cell imaging of Hoechst 33342 and BDL-F2 dye-stained RPE1 cells was conducted with confocal microscopy (100×; Nikon, Tokyo, Japan). Analysis of confocal images showed the distribution of the BDL-F2 dye which resembles the cytoplasm inside the cell (FIG. 8). Confocal imaging was performed with Nikon A1R+ Confocal microscope. RPE1 cells were seeding in 35 mm glass bottom dish, BDL-F2 (1 µM) stained-cells were taken with confocal microscope. 100× objective lens (Nikon) was used to visualize cells. Laser excitation light was provided at a wavelength of 570 nm, and fluorescent emissions were collected at wavelengths above 562 nm.

Example 8

Time Lapse Images

Time lapse imaging was performed with Nikon Ti inverted microscope and Nikon Biostation IM. RPE1:H2B:GFP cells were seeded in 35 mm dish, BDL-F2 (400 nM)-treated cells were stained for 8 h or 50 h for long term experiments. At the same time, BDL-F2 stained cells were monitored for 8 h via fluorescence microscopy through Nikon Ti inverted microscope with a CoolSNAP HQ digital camera and 50 hby Nikon Biostation IM. These data are representative of at least three independent experiments.

Figure 3:
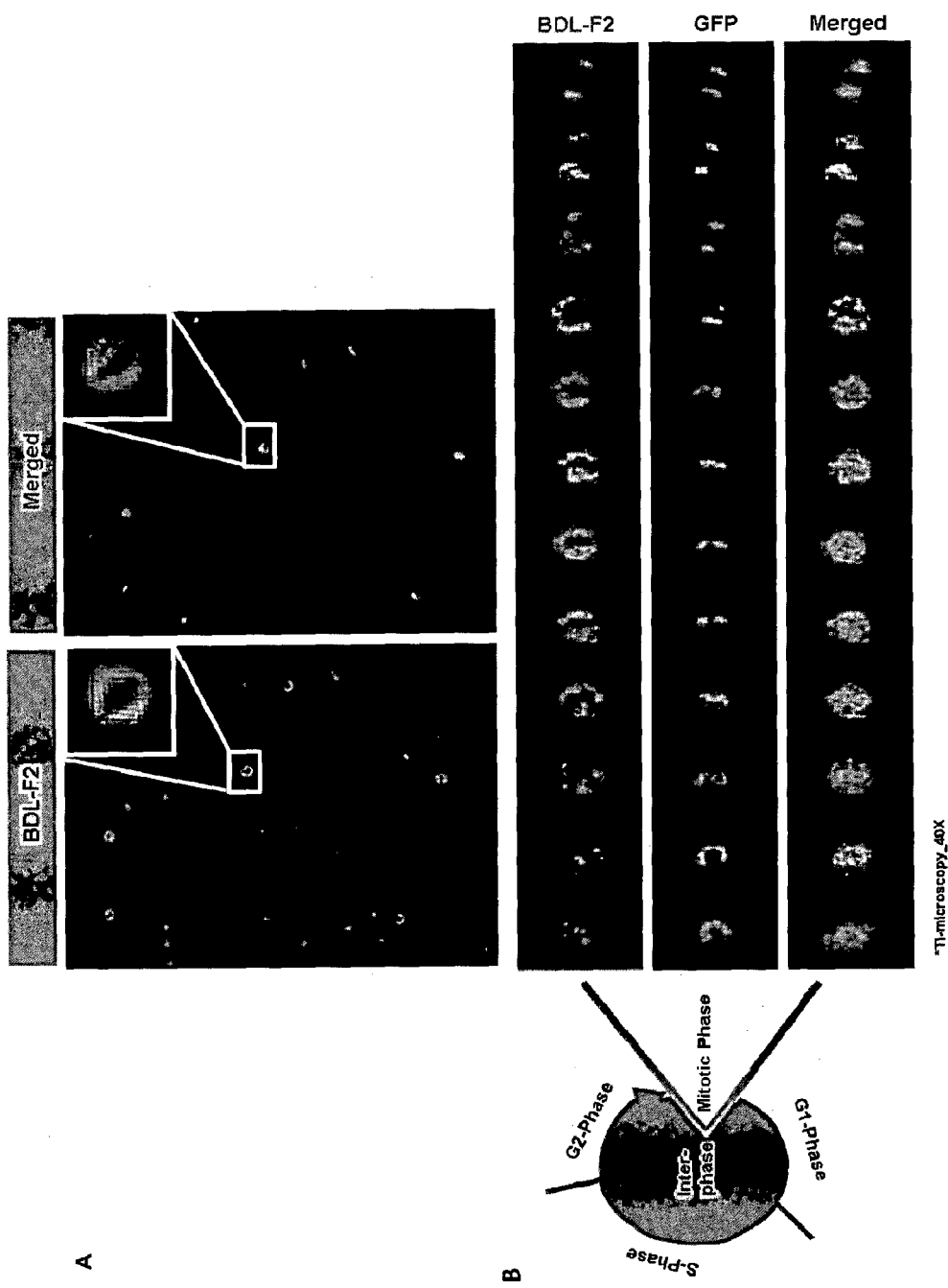
FIG. 3 shows monitoring the M-phase progression in live cells with BDL-F2.
Figure 9:
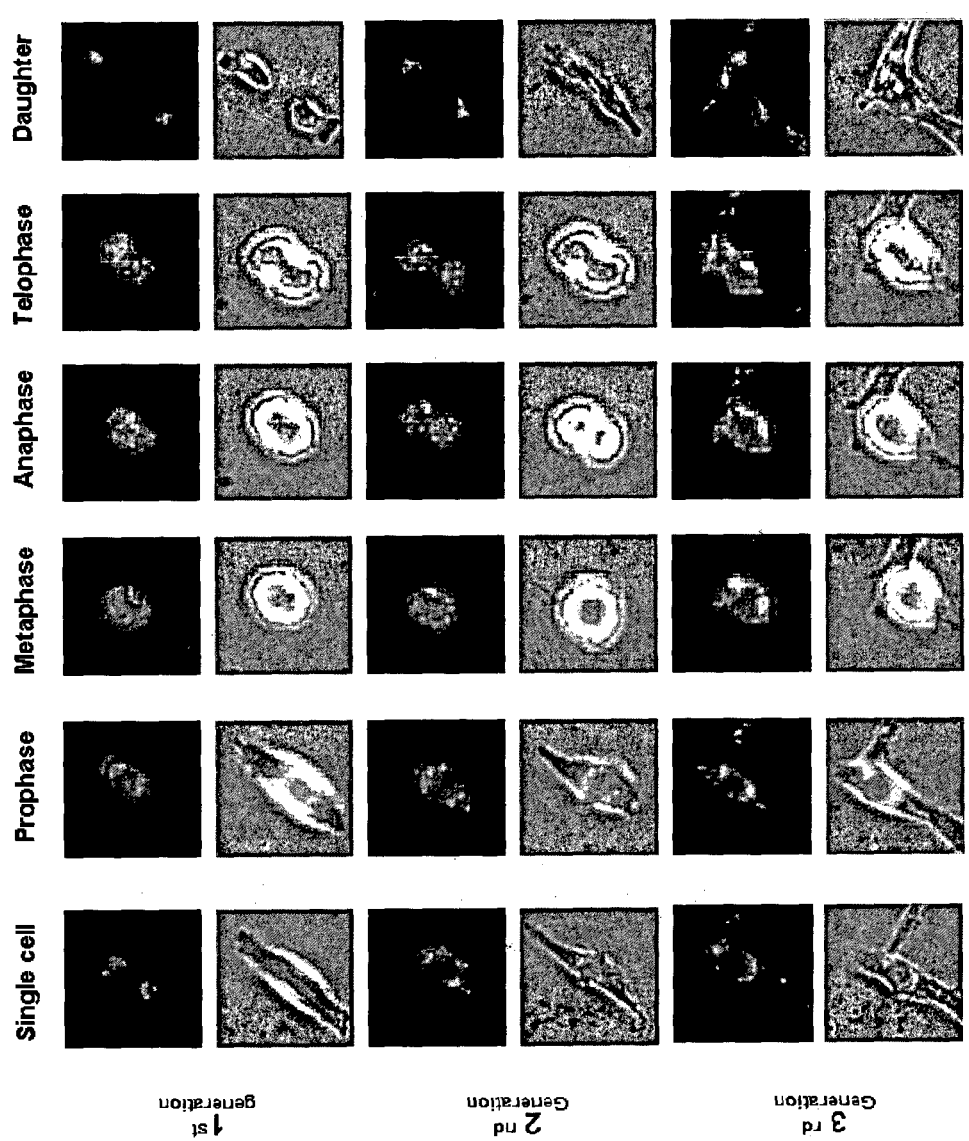
FIG. 9 shows cell proliferation over the course of a long-term live imaging experiment, utilizing the BDL-F2 dye. Time-lapse imaging of a BDL-F2-stained cell showed direct cytoplasm dynamics of M-phase progress for 50 h. Specifically, first generation is shown in the upper panel; second generation is shown in the middle panel; and third generation is shown in the lower panel. BDL-F2 stains the mitotic cells a yellow color. Imaging with Nikon Biostation IM, 10×.

The subcellular pattern of BDL-F2 staining was examined to determine if it could distinguish specific mitosis, by comparing the H2B-GFP expression. Time-lapse imaging illustrated a fluctuation of the BDL-F2 signal in cytoplasm of mitotic RPE1:H2B:GFP cells. BDL-F2 was visible during mitotic progression. These observations demonstrated that BDL-F2 enables the real time visualization of fluorescence in live mitotic cells with or without Tubulyzine B (FIG. 3). BDL-F2 was then utilized in a long term time lapse experiment in order to monitor cell proliferation. As shown in FIG. 9, BDL-F2 enables the visualization of three generations of proliferating cells, without demonstrating any cytotoxicity.

Overall, the findings presented herein suggest that BDL-F2 provides a convenient approach for assigning the development of detailed predictive models of cell cycle progression in addition to its use for developmental biology and regenerative approaches testing small molecules and factors modulating the cell cycle.

REFERENCES

1. Karolin, J., et al., *J. Am. Chem. Soc.* 1994, 116, 7801-7806.
2. Zhai D., et al., *ACS Comb. Sci.* 2012, 14, 81.
3. Kanda T., Sullivan K. F., Wahl G. M. *Curr. Biol.* 1998, 8, 377.
4. Crosio, C., et al. *Mol. Cell. Biol.* 2002; 22(3): 874-885.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A compound having the structure of Formula (I) or a pharmaceutically acceptable salt thereof:

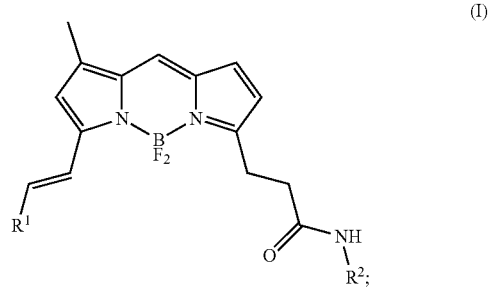

(I)

wherein:

$R^1$ is $(C_6$-$C_{10})$aryl or $(C_3$-$C_{12})$heteroaryl, optionally substituted at any position with one or more substituents independently selected from $(C_1$-$C_{10})$alkyl, —O($C_1$-$C_6$)alkyl, $(C_2$-$C_6$)alkenyl, $(C_6$-$C_{10})$aryl, —O($C_6$-$C_{10}$)aryl, —S($C_1$-$C_{10}$)alkyl, —O(benzyl), $(C_3$-$C_8$)heteroaryl, halo, hydroxyl, —NR$^3$R$^4$, nitro or —O($C_2$-$C_6$)alkenyl;

further wherein each —O($C_1$-$C_6$)alkyl, $(C_2$-$C_6$)alkenyl, —O($C_6$-$C_{10}$)aryl, —O(benzyl) or $(C_3$-$C_8$)heteroaryl is optionally substituted at any position with one or more substituents independently selected from halo, $(C_6$-$C_{10})$aryl, $(C_1$-$C_{10})$alkyl or —O($C_1$-$C_6$)alkyl;

$R^2$ is $(C_1$-$C_6$)alkyl or $(C_3$-$C_8$)cycloalkyl, optionally and independently substituted with one or more substituents selected from —NR$^5$R$^6$, hydroxyl, halo or —O($C_1$-$C_6$)alkyl; and $R^3$, $R^4$, $R^5$, and $R^6$, if present, are independently selected from H, $(C_1$-$C_6$)alkyl, $(C_6$-$C_{10})$aryl, $(C_1$-$C_6$)hydroxyalkyl, or are taken together to form a $(C_3$-$C_7)$heterocycle.

2. The compound of claim 1, wherein $R^1$ is $(C_6$-$C_{10})$aryl, optionally substituted at any position with one or more substituents independently selected from $(C_1$-$C_{10})$alkyl or —O($C_1$-$C_6$)alkyl; and $R^2$ is $(C_1$-$C_6$)alkyl, optionally substituted with one or more substituents independently selected from —NR$^5$R$^6$ or hydroxyl.

3. The compound of claim 1, having the structure of Formula (II), or a pharmaceutically acceptable salt thereof:

(II)
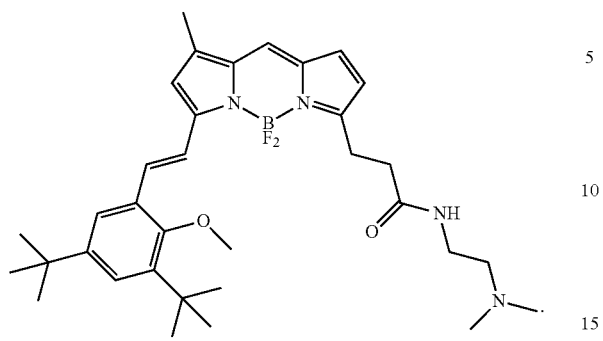
(VII)
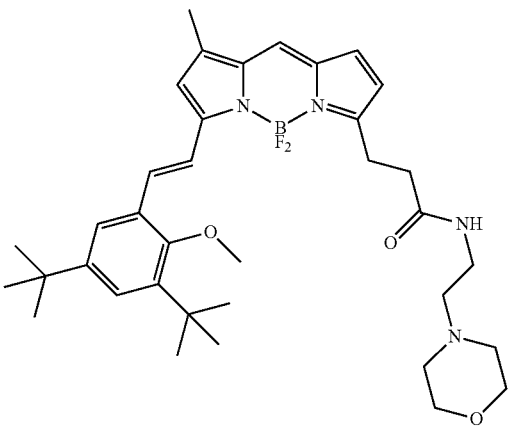
4. The compound of claim 2, having the structure of any one of Formulae (IV), (V), (VI), (VII), (VIII), (IX), (X), (XI) or (XII), or a pharmaceutically acceptable salt thereof:
(IV) (VIII)
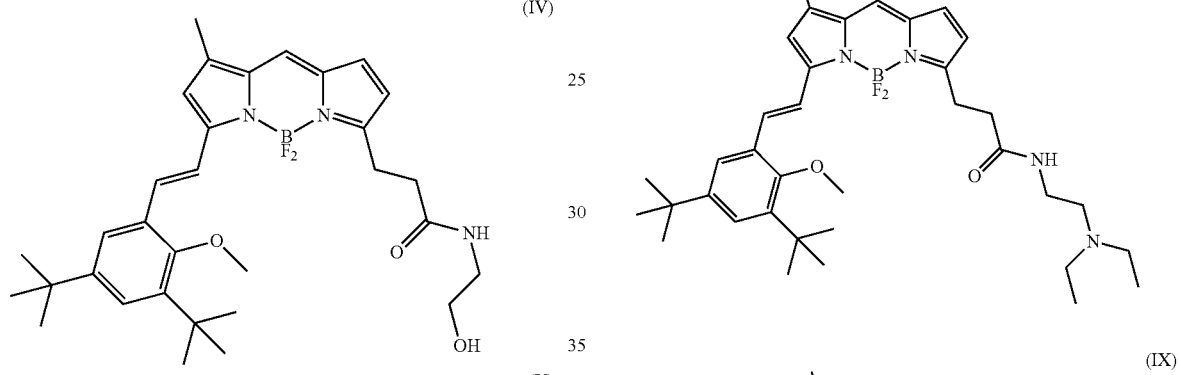
(V) (IX)
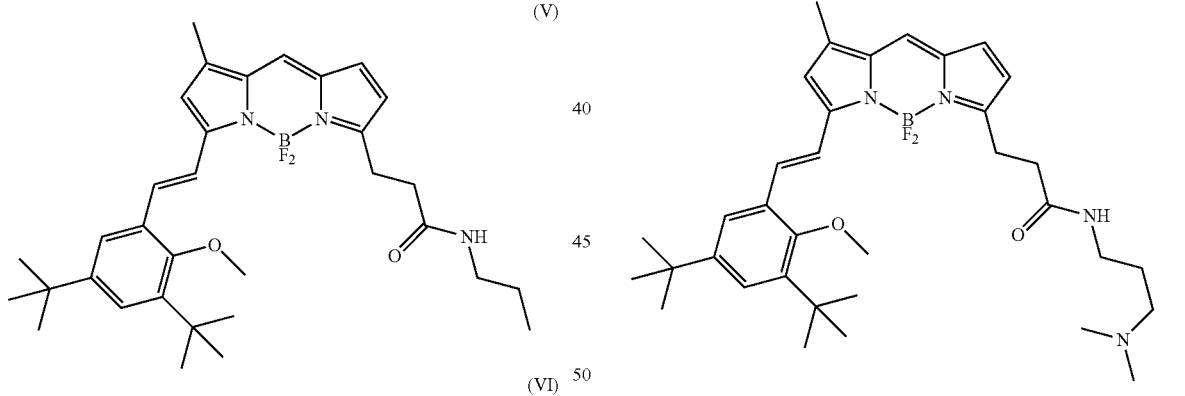
(VI) (X)
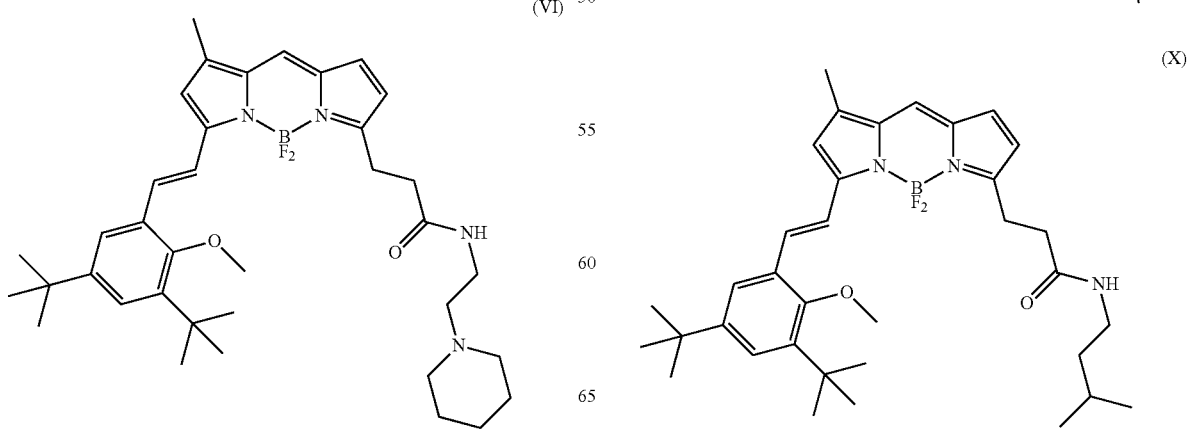

-continued

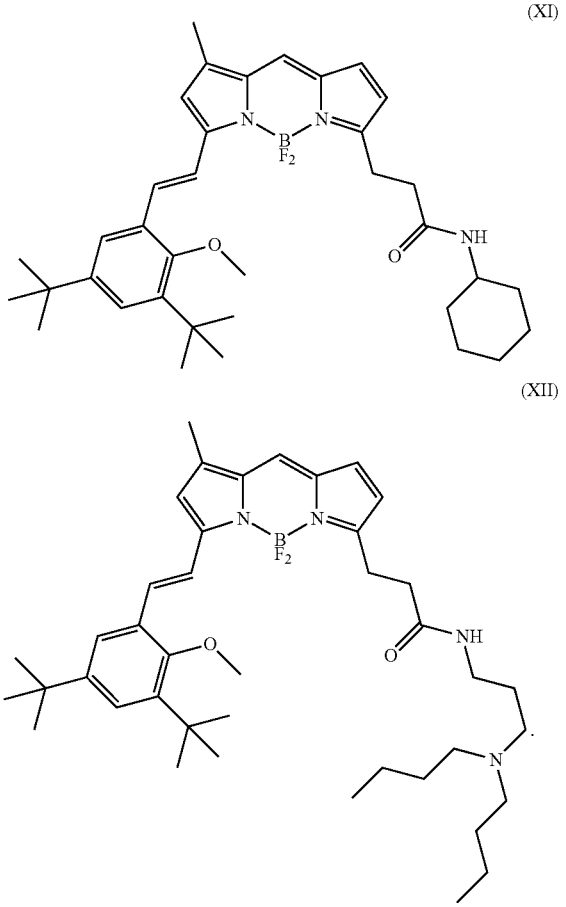

5. A method for the synthesis of a compound of Formula (I) or a pharmaceutically acceptable salt thereof:

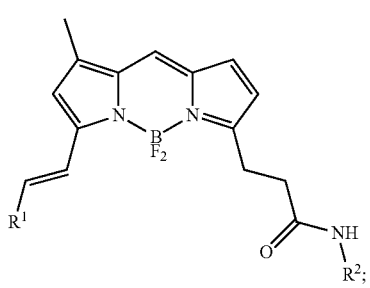

wherein:
R¹ is (C₆-C₁₀)aryl or (C₃-C₁₂)heteroaryl, optionally substituted at any position with one or more substituents independently selected from (C₁-C₁₀)alkyl, —O(C₁-C₆)alkyl, (C₂-C₆)alkenyl, (C₆-C₁₀)aryl, —O(C₆-C₁₀)aryl, —S(C₁-C₁₀)alkyl, —O(benzyl), (C₃-C₈)heteroaryl, halo, hydroxyl, —NR³R⁴, nitro or —O(C₂-C₆)alkenyl;
further wherein each —O (C₁-C₆)alkyl, (C₂-C₆)alkenyl, —O(C₆-C₁₀)aryl, —O(benzyl) or (C₃-C₈)heteroaryl is optionally substituted at any position with one or more substituents independently selected from halo, (C₆-C₁₀)aryl, (C₁-C₁₀)alkyl or —O(C₁-C₆)alkyl;

R² is (C₁-C₆)alkyl or (C₃-C₈)cycloalkyl, optionally and independently substituted with one or more substituents selected from —NR⁵R⁶, hydroxyl, halo or —O(C₁-C₆)alkyl; and
R³, R⁴, R⁵, and R⁶, if present, are independently selected from H, (C₁-C₆)alkyl, (C₆-C₁₀)aryl, (C₁-C₆)hydroxyalkyl, or are taken together to form a (C₃-C₇)heterocycle;
the method comprising:
reacting a compound of Formula (III):

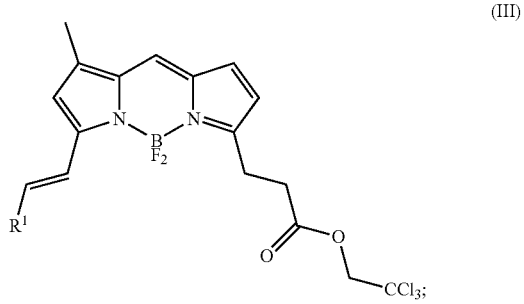

with a compound having the formula R²NH₂, thereby forming a compound of Formula (I).

6. The method of claim 5, wherein the compound of Formula (I) has a structure of Formula (II), or a pharmaceutically acceptable salt thereof:

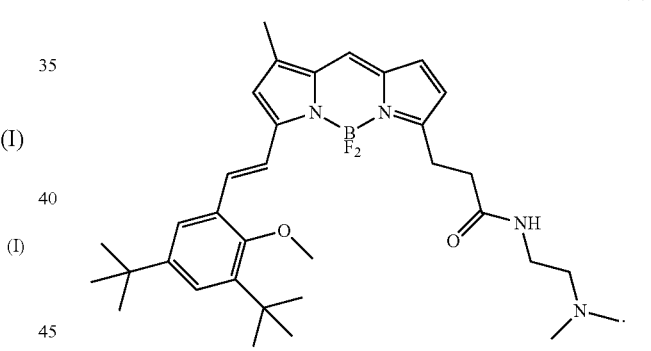

7. The method of claim 5, wherein the compound of Formula (I) has a structure of any one of Formulae (IV), (V), (VI), (VII), (VIII), (IX), (X), (XI), or (XII) or a pharmaceutically acceptable salt thereof:

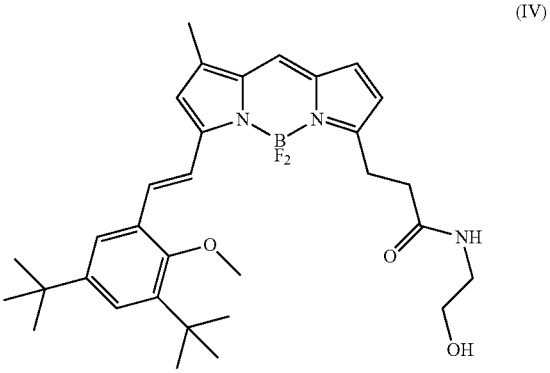

(V)
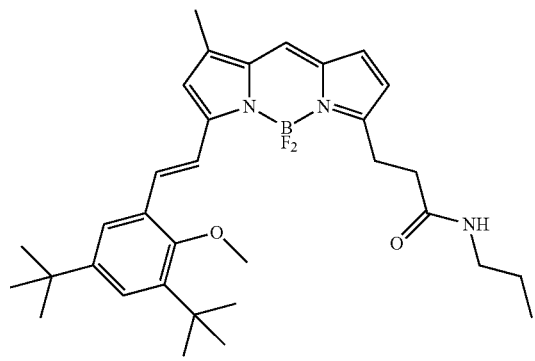
(VI)
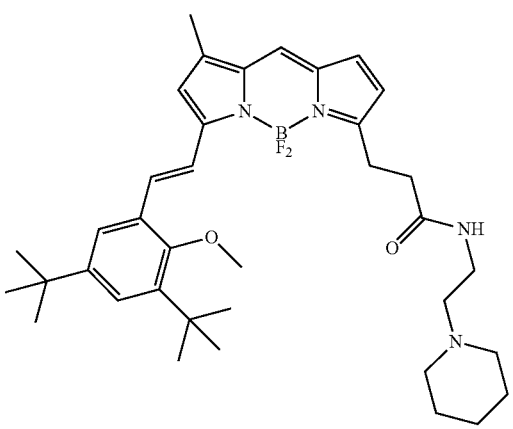
(VII)
(VIII)
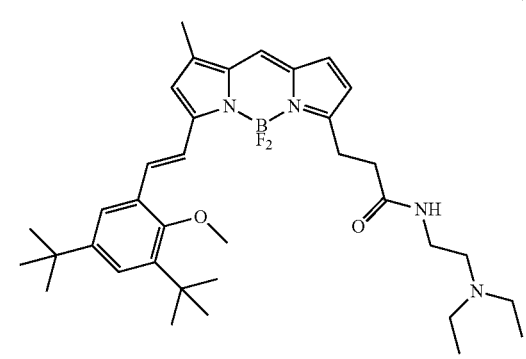
(IX)
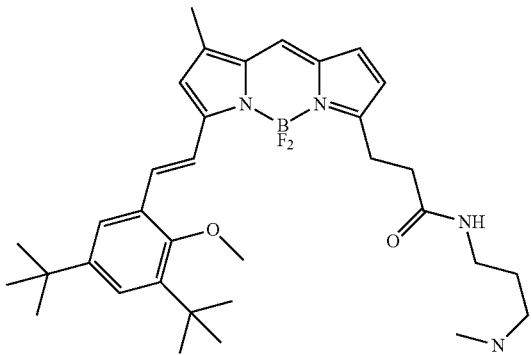
(X)
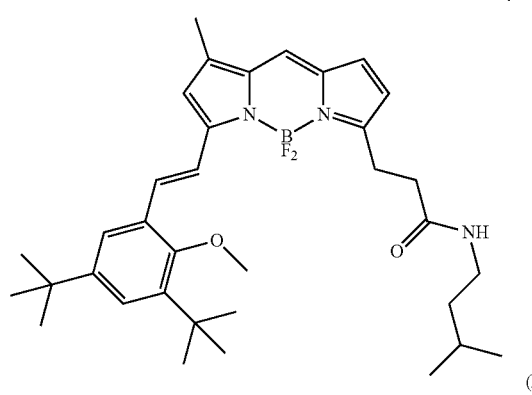
(XI)
(XII)
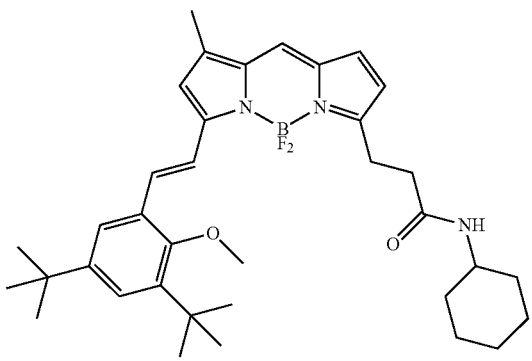

8. A method for assessing the progression of mitosis in a live cell, comprising:
(a) contacting a live cell with a compound of formula (I),

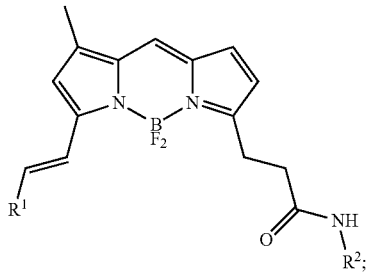

(I)

wherein:
R$^1$ is (C$_6$-C$_{10}$)aryl or (C$_3$-C$_{12}$)heteroaryl, optionally substituted at any position with one or more substituents independently selected from (C$_1$-C$_{10}$)alkyl, —O(C$_1$-C$_6$)alkyl, (C$_2$-C$_6$)alkenyl, (C$_6$-C$_{10}$)aryl, —O(C$_6$-C$_{10}$)aryl, —S(C$_1$-C$_{10}$)alkyl, —O(benzyl), (C$_3$-C$_8$)heteroaryl, halo, hydroxyl, —NR$^3$R$^4$, nitro or —O(C$_2$-C$_6$)alkenyl;
further wherein each —O(C$_1$-C$_6$)alkyl, (C$_2$-C$_6$)alkenyl, —O(C$_6$-C$_{10}$)aryl, O(benzyl) or (C$_3$-C$_8$)heteroary is optionally substituted at any position with one or more substituents independently selected from halo, (C$_6$-C$_{10}$)aryl, (C$_1$-C$_{10}$)alkyl or —O(C$_1$-C$_6$)alkyl;
R$^2$ is (C$_1$-C$_6$)alkyl or (C$_3$-C$_8$)cycloalkyl, optionally and independently substituted with one or more substituents selected from —NR$^5$R$^6$, hydroxl, halo or —O(C$_1$-C$_6$)alkyl; and
R$^3$, R$^4$, R$^5$, and R$^6$, if present, are independently selected from H, (C$_1$-C$_6$)alkyl, (C$_6$-C$_{10}$)aryl, (C$_1$-C$_6$)hydroxyalkyl, or are taken together to form a (C$_3$-C$_7$)heterocycle;
or a pharmaceutically acceptable salt thereof;
to form an incubation media;
b) incubating the incubation media of step (a) for a period of time to stain the live cell; and
c) imaging the stained cell of step (b) to assess the progression of mitosis in the live cell by fluorescence microscopy.

9. The method of claim 8, wherein R$^1$ is (C$_6$-C$_{10}$)aryl, optionally substituted at any position with one or more substituents independently selected from (C$_1$-C$_{10}$)alkyl or —O(C$_1$-C$_6$)alkyl; and R$^2$ is (C$_1$-C$_6$)alkyl, optionally substituted with one or more substituents independently selected from —NR$^5$R$^6$.

10. The method of claim 9, wherein the compound of Formula (I) has the structure of Formula (II), or a pharmaceutically acceptable salt thereof:

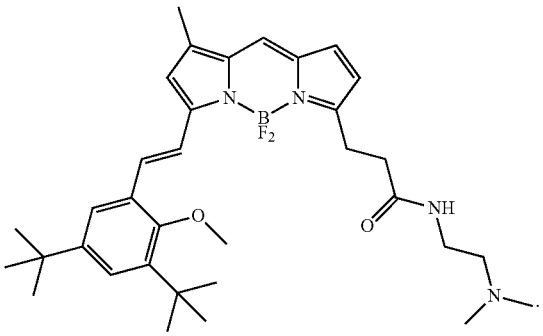

(II)

11. A method for the preferential staining of an M-phase live cell, comprising:
contacting a live cell with a compound of formula (I) of claim 1, or a pharmaceutically acceptable salt thereof; to form an incubation media;
b) incubating the incubation media of step (a) for a period of time to stain the M-phase live cell; and
c) visualizing the stained M-phase live cell of step (b) with microscopy, wherein a live cell that exists in the M-phase is stained with higher intensity than a live cell that exists in any other phase of the cell cycle.

12. The method of claim 11, wherein R$^1$ is (C$_6$-C$_{10}$)aryl, optionally substituted at any position with one or more substituents independently selected from (C$_1$-C$_{10}$)alkyl or —O(C$_1$-C$_6$)alkyl; and R$^2$ is (C$_1$-C$_6$)alkyl, optionally substituted with one or more substituents independently selected from —NR$^5$R$^6$.

13. The method of claim 12, wherein the compound of Formula (I) has the structure of Formula (II), or a pharmaceutically acceptable salt thereof:

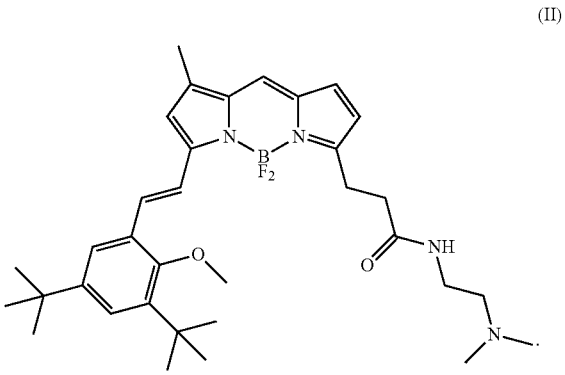

(II)

* * * * *